United States Patent [19]

Ferrini et al.

[11] 3,960,868
[45] June 1, 1976

[54] DERIVATIVES OF 6,7 OR 8 CYCLOALKYL 4-OXO QUINOLINE 3 CARBOXYLIC ACID

[75] Inventors: Pier Giorgio Ferrini, Binningen; Georges Haas; Alberto Rossi, both of Oberwil, all of Switzerland

[73] Assignee: Ciba-Geigy Corporation, Ardsley, N.Y.

[22] Filed: May 6, 1974

[21] Appl. No.: 467,166

[30] Foreign Application Priority Data

May 11, 1973  Switzerland.......................... 6722/73
Mar. 21, 1974  Switzerland.......................... 3935/74

[52] U.S. Cl. .................. 260/287 AN; 260/283 SY; 260/471 R; 260/558 P; 424/258
[51] Int. Cl.² ..................................... C07D 215/56
[58] Field of Search .................. 260/287 R, 287 AN

[56] References Cited
UNITED STATES PATENTS

| | | | |
|---|---|---|---|
| 3,452,026 | 6/1969 | Perron et al. .................. | 260/287 R |
| 3,506,667 | 4/1970 | Kaminsky....................... | 260/287 R |
| 3,542,851 | 11/1970 | Patchett et al.................. | 260/287 R |
| 3,761,592 | 9/1973 | Mizzoni et al. ..................... | 424/258 |
| 3,849,421 | 11/1974 | Nakagome et al. .............. | 260/287 R |

FOREIGN PATENTS OR APPLICATIONS 830,832  3/1960  United Kingdom................. 210/287

Primary Examiner—Alton D. Rollins
Assistant Examiner—David E. Wheeler
Attorney, Agent, or Firm—Joseph G. Kolodny; Theodore O. Groeger; John J. Maitner

[57] ABSTRACT

Quinolines of the formula I

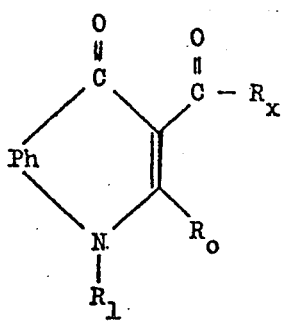

and of the formula X

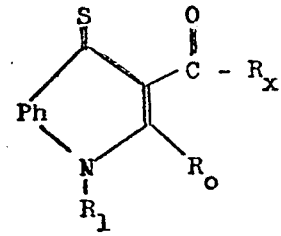

or

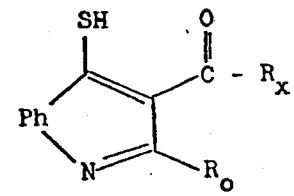

or

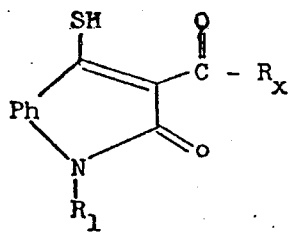

(X)

wherein Ph denotes a 1,2-phenylene radical which carries cycloaliphatic radical, $R_x$ denotes a free or etherified hydroxyl group or a free or substituted amino group, $R_o$ denotes an alkyl radical, a free hydroxyl group or a hydroxyl group etherified by lower alkyl or, above all, a hydrogen atom and $R_1$ denotes an aliphatic or cycloaliphatic hydrocarbon radical which is optionally substituted by hydroxyl, an araliphatic radical or a hydrogen atom, and their salts, which possess valuable analgesic, anti-inflammatory, anti-microbial and histamine liberation inhibiting properties.

11 Claims, No Drawings

DERIVATIVES OF 6,7 OR 8 CYCLOALKYL 4-OXO QUINOLINE 3 CARBOXYLIC ACID

The invention relates to new quinolines of the formula I

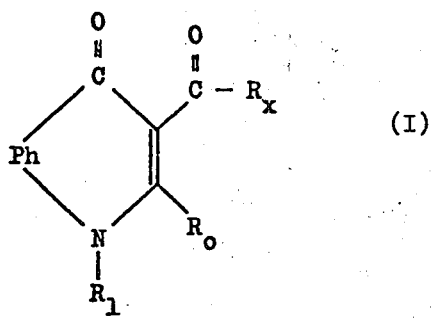

wherein Ph denotes a 1,2-phenylene radical which carries a cycloaliphatic radical, $R_x$ denotes a free or etherified hydroxyl group or a free or substituted amino group, $R_o$ denotes an alkyl radical, a free hydroxyl group or a hydroxyl group etherified by lower alkyl or, above all, a hydrogen atom, and $R_1$ denotes an aliphatic or cycloaliphatic hydrocarbon radical which is optionally substituted by hydroxyl, an araliphatic radical or a hydrogen atom, and to their salts and processes for the manufacture of these compounds.

The cycloaliphatic radical is above all a saturated or singly unsaturated cycloalkyl radical, above all with 3 to 10, especially 5 to 8, ring members. Radicals to be mentioned above all are cycloalkyl radicals with 3 to 10 ring members, such as cyclopropyl, cyclopentyl, cyclohexyl, cycloheptyl, cyclooctyl, cyclononly or cyclodecyl radicals and also cycloalkenyl radicals with 5 to 8 ring members, such as 3-cyclohexenyl or 4-cycloheptenyl radicals or, in particular, corresponding 1-cycloalkenyl radicals, such as 1-cyclopentenyl, 1-cyclohexenyl, 1-cycloheptenyl or 1-cyclooctenyl radicals, and also an adamantyl radical.

The cycloaliphatic radicals can be substituted or unsubstituted. Possible substituents are above all lower alkyl radicals, above all methyl, hydroxyl groups, lower alkoxy groups, above all methoxy, lower alkenyloxy groups, oxo groups, acyloxy groups or halogen. Accordingly, the following may be mentioned as examples of substituted cycloaliphatic radicals: 6-Methyl-1-cyclohexenyl, 2-methyl-1-cyclohexenyl, 4-methyl-1-cyclohexenyl, 4-methoxy-1-cyclohexenyl, 2-hydroxy-cyclohexyl, 2-hydroxy-cycloheptyl or -cyclooctyl, 4-methoxy-cycloheptyl or -cyclooctyl, 2-methyl-cyclohexyl, 4-methyl-cyclohexyl, 4-methoxy-cyclohexyl, 4-oxocyclohexyl, 4-chloro-cyclohexyl, 4-fluoro-cyclohexyl, 2-chloro-cyclohexyl, 2-fluoro-cyclohexyl, 4chloro-cyclohexen-1-yl and 4-fluoro-cyclohexen-1-yl, as well as the corresponding bromine compounds.

The 1,2-phenylene radical Ph which has been mentioned can contain yet further substituents. Thus it can be substituted in those of the positions 3 to 6 in which the cycloaliphatic radical is not present. Possible substituents are above all lower alkyl radicals, lower alkoxy groups, halogen atoms, above all chlorine, trifluoromethyl groups, nitro groups or amino groups.

Etherified hydroxyl groups $R_x$ are preferably hydroxyl groups substituted by aliphatic hydrocarbon radicals, above all alkoxy radicals, such as lower alkoxy radicals, or alkenyloxy radicals, such as lower alkenyloxy radicals. Methoxy, ethoxy and allyloxy radicals should be singled out particularly.

Substituted amino groups $R_x$ are, above all, secondary or tertiary amino groups, especially amino groups which are monosubstituted or disubstituted by aliphatic, aromatic or araliphatic radicals. Preferred aliphatic radicals are lower aliphatic hydrocarbon radicals which can also be interrupted in the carbon chain by hetero-atoms, such as oxygen, sulphur or nitrogen atoms, and/or be substituted, for example by hydroxyl groups. Preferred aromatic radicals are, in particular, phenyl radicals which can be substituted by lower alkyl, lower alkoxy, trifluoromethyl or halogen.

Preferred araliphatic radicals are, in particular, phenyl-lower alkyl radicals with 1 to 6 C atoms in the lower alkyl part, it being possible for the phenyl radical to be substituted by lower alkyl, lower alkoxy, trifluoromethyl or halogen.

Possible substituents of the amino group are, in particular: Lower alkyl radicals, lower alkenyl radicals, lower hydroxyalkyl radicals, alkylene radicals, such as butylene-(1,4), pentylene-(1,5), hexylene-(1,5), hexylene-(1,6), hexylene-(2,5), heptylene-(1,7), heptylene-(2,7) or heptylene-(2,6) radicals, or oxa-alkylene, aza-alkylene or thia-alkylene radicals in which the hetero-atoms are separated by at least 2 carbon atoms and which preferably together with the amine nitrogen atom form an at most 8-membered ring, such as 3-oxa-pentylene-(1,5), 3-thiapentylene-(1,5), 2,4-dimethyl-3-thia-pentylene-(1,5), 3-aza-pentylene-(1,5), 3-lower alkyl-3-azapentylene-(1,5), such as 3-methyl-3-aza-pentylene-(1,5), 3-(hydroxy-lower alkyl)-3-aza-pentylene-(1,5), such as 3-($\beta$-hydroxyethyl)-3-aza-pentylene-(1,5), 3-oxa-hexylene-(1,6) or 3-azahexylene-(1,6) radicals, optionally substituted phenyl radicals or phenyl-lower alkyl radicals, such as benzyl or phenylethyl radicals.

An amino group $R_x$ is thus, for example, a mono- or di-lower alkylamino group, such as a methylamino, ethylamino, propylamino, butylamino, isopropylamino, sec.-butylamino, dimethylamino, diethylamino, N-methyl-N-ethylamino, dipropylamino, diisopropylamino, dibutylamino, di-sec.-butylamino or diamylamino group or an optionally C-lower alkylated pyrrolidino, piperidino, piperazino, N'-lower alkyl-piperazino or N'-(hydroxy-lower alkyl)-piperazino, thiomorpholino or morpholino group or an optionally substituted anilino group, such as, for example, a p-halogenoanilino group or a benzylamino or 2-phenylethylamino group or above all an unsubstituted amino group.

An aliphatic hydrocarbon radical is above all an alkyl radical or an alkenyl radical, for example a lower alkenyl radical. An alkyl radical is above all a lower alkyl radical.

A lower alkyl radical is, in particular, an alkyl radical with at most 8 carbon atoms, such as, for example, a methyl, ethyl, propyl or isopropyl radical or a straight or branched butyl, pentyl or hexyl radical bonded in any desired position.

A lower alkenyl radical is, for example, an alkenyl radical with at most 8 carbon atoms, such as, in particular, an allyl or methallyl radical.

An aliphatic hydrocarbon radical substituted by hydroxyl is, for example, a lower hydroxyalkyl radical, such as, above all, a hydroxyalkyl radical with at most 8 carbon atoms, in which the hydroxyl group is separated from the linkage point by at least 2 carbon atoms, such as, for example, a β-hydroxyethyl, β-hydroxypropyl, γ-hydroxypropyl or δ-hydroxybutyl radical.

A cycloaliphatic hydrocarbon radical $R_1$ is, for example, a cycloalkyl radical with, preferably, 3-8, especially 5-8, ring members, or a cycloalkenyl radical with, preferably, 5-8 ring members, such as a cyclopropyl, cyclobutyl, cyclopentyl, cyclohexyl or cycloheptyl radical, or one of the abovementioned cycloalkenyl radicals.

An araliphatic radical is above all a phenyl-lower alkyl radical, such as, for example, a benzyl, α-phenylethyl or β-phenylethyl radical, wherein the phenyl radical can also carry one, two or more substituents, for example lower alkyl radicals, lower alkoxy groups, lower alkenyloxy groups, halogen atoms, trifluoromethyl groups, nitro groups and/or amino groups.

Lower alkoxy groups are, for example, methoxy, ethoxy, propoxy, isopropoxy or butoxy groups and possible halogen atoms are above all fluorine, chlorine or bromine atoms.

Lower alkenyloxy groups are above all those which are derived from the said lower alkenyl radicals, especially allyloxy and methallyloxy groups.

Acyloxy groups are above all those in which the acyl radical is the radical of a carboxylic acid. Above all they can be the radicals of lower fatty acids, such as of lower alkanecarboxylic or lower alkenecarboxylic acids, for example propionic acid, butyric acid, trimethylacetic acid, acrylic acid, valeric acid and above all acetic acid. Further possible acyl radicals are the radicals of aromatic or araliphatic carboxylic acids, such as of benzoic acids or phenyl-lower alkanecarboxylic acids or phenyl-lower alkenecarboxylic acids, for example phenylacetic acids, phenylpropionic acid or cinnamic acids, wherein the aromatic nuclei can also be substituted, for example as indicated above for the araliphatic radicals.

Those of the new compounds in which $R_1$ represents hydrogen can also be in their tautomeric form, that is to say in the form of compounds of the formula II

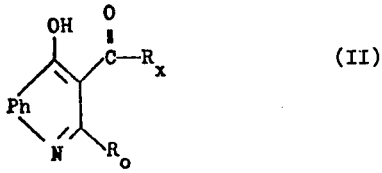

wherein $R_o$, $R_x$ and Ph have the indicated meanings.

Those of the new compounds in which $R_o$ is a hydroxyl group can be in a further tautomeric form, namely as compounds of the formula III

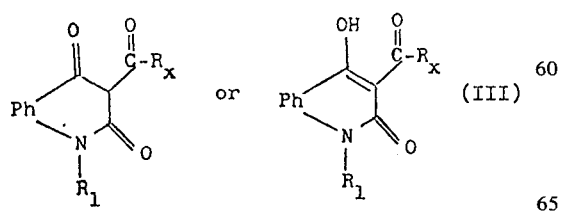

wherein $R_1$, $R_x$ and Ph have the indicated meaning.

The new compounds possess valuable pharmacological properties, above all an analgesic, such as anti-nociceptive, action, and an anti-inflammatory action, coupled with low toxicity. Thus, for example, they show an anti-nociceptive action in the writhing syndrome test (phenyl-p-benzoquinone) in mice on oral administration in a dose of 1 – 100 mg/kg, and an anti-inflammatory action in the kaolin oedema test on the paws of rats on oral administration of a dose of 1 – 100 mg/kg. The compounds therefore are useful as analgesics, and especially as antiphlogistics.

The new compounds further possess valuable anti-microbial, especially anti-bacterial, fungistatic, anti-viral and coccidiostatic properties.

Thus, for example, the new compounds show, in incorporation tests [X. Bühlmann, W. A. Vischer and H. Bruhin, Zbl. Bakt. Section I, Originals, 180 327–334 (1960)], in concentrations from about 0.2 µg/ml, an activity against a large number of Gram-positive and Gram-negative bacteria, such as Staphylococcus aureus, Bacillus subtilis, Escherichia coli, Proteus vulgaris, Pseudomonas aeruginosa, Klebsiella pneumonia, Salmonella typhimurium, Streptococcus faecalis and Shigella sonnei. The anti-bacterial activity of the new compounds can also be demonstrated in vivo, for example by injection experiments on mice, where an excellent action is found both on subcutaneous and on peroral administration. Because of the said acitivities the new compounds can be employed both in systemic infections, for example in infections of the urinary tracts, and for protecting materials against microbes.

The fungistatic activity of the new compounds can be demonstrated in the abovementioned incorporation tests, where an action manifests itself from about 10 µg/ml, for example against Microsporum canis, Trichophyton mentagrophytes, Sporrotrichum schenckii and Aspergillus fumigatus.

The anti-viral action of the new compounds can also be demonstrated in animal experiments. For example, the mean life is increased, in comparison to controls, in the case of mice infected with Coxsackie virus $B_1$, when using peroral doses of about 125 to about 500 mg/kg, and in mice infected with Herpes simplex when using peroral doses of about 250 to 500 mg/kg. The new compounds therefore are useful as anti-microbial agents.

The new compounds further possess a histamine liberation inhibiting action, as can be demonstrated in vitro in doses of about 0.003 to 0.030 mg/ml in the histamine liberation test on peritoneal cell suspensions of rats using [D-Ser$^1$, Lys$^{17,18}$]-β-corticotropin-(1-19)-nonadecapeptide n-tetradecyl ester acetate [R. Jaques and M. Brugger, Pharmacology 2, 361-370, (1969); M. Brugger, Helv. Chim. Acta. 54, 1261-1274, (1971)] and therefore are useful as anti-allergic agents.

However, the new compounds are also valuable intermediate products for the manufacture of other useful materials, especially of pharmacologically active compounds.

Compounds to be particularly singled out are those of the formula Ia (Ia)

or of its tautomeric form, wherein $R_o$, $R_1$ and $R_x$ have the abovementioned meanings, $R_2$ occupies position 6, 7 or 8 and represents a cycloalkyl or cycloalkenyl radical with 5–8 ring members, which can also be substituted by lower alkyl, lower alkoxy, oxo, hydroxyl or lower alkanoyl, or represents the 1-adamantyl radical, and $R_3$ occupies any desired free position of the 1,2-phenylene radical and denotes lower alkyl, lower alkoxy or above all halogen or hydrogen.

Compounds to be singled out especially are those of the formula Ia or of its tautomeric form, wherein $R_2$, $R_3$ and $R_1$ have the above meanings and $R_o$ represents hydrogen, lower alkyl with up to 4 C atoms, hydroxyl or lower alkoxy and $R_x$ denotes hydroxyl, lower alkoxy or an optionally substituted amino group.

Compounds to be singled out above all are those of the formula Ia or of its tautomeric form wherein $R_2$ occupies positions 6, 7 or 8 of the quinoline skeleton and denotes cycloalkyl with 5 to 8 ring members, cycloalkenyl with 5–7 ring members or 1-adamantyl, $R_3$ occupies any desired free position of the 1,2-phenylene radical and represents hydrogen, lower alkyl, lower alkoxy or halogen, $R_1$ denotes hydrogen, lower alkyl, lower alkenyl or aryl-lower alkyl, $R_o$ represents hydrogen, lower alkoxy or hydroxyl and $R_x$ denotes hydroxyl, lower alkoxy or an optionally substituted amino group.

Compounds to be singled out very particularly are those of the formula Ia or of its tautomeric form wherein $R_2$ occupies positions 6, 7 or 8 of the quinoline skeleton and denotes cycloalkyl with 5 to 8 ring members, cycloalkenyl with 5–8 ring members or 1-adamantyl, $R_3$ can occupy one of the free positions of the 1,2-phenylene radical and represents hydrogen, halogen or lower alkoxy with up to 4 C atoms, $R_1$ denotes hydrogen, lower alkyl with up to 6 C atoms, lower alkenyl with 3–4 C atoms or aryl-lower alkyl with up to 3 C atoms in the lower alkyl part, $R_o$ represents hydrogen or hydroxyl and $R_x$ denotes hydroxyl, lower alkoxy with 1–3 C atoms or optionally substituted anilino, and in particular $R_2$ is cyclopentyl, cyclohexyl, cycloheptyl, cyclohexen-1-yl, cyclooctyl or 1-adamantyl, $R_3$ is hydrogen, chlorine or methoxy, $R_1$ represents hydrogen, methyl, ethyl, hexyl, allyl or benzyl, $R_o$ is hydrogen or hydroxyl and $R_x$ represents hydroxyl, methoxy, ethoxy or p-chloroanilino, and very particularly the compounds mentioned in the examples.

The new compounds are obtained according to methods which are in themselves known.

A preferred procedure is the intramolecular condensation, with elimination of $HZ_o$, of a compound of the formula IV

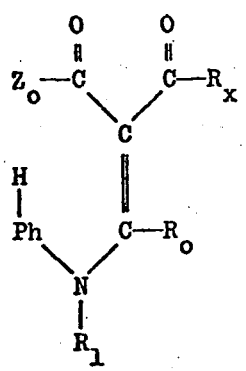

(IV)

wherein Ph, $R_x$, $R_o$ and $R_1$ have the indicated meanings and $Z_o$ denotes a removable radical, or of a tautomer of such a compound, in which $R_1$ represents hydrogen.

The radical of the formula

is, in particular, a functionally modified carboxyl group containing an oxo group, such as a halogenocarbonyl group, an acid anhydride group or, above all, an esterified carboxyl group. If the radicaal $Z_o$ is a halogen atom, it is above all a chlorine atom. If $Z_o$ is an acyloxy group, it is, for example, a lower alkanoyloxy group, such as the acetoxy group, or above all an alkoxycarbonyloxy group, such as a lower alkoxycarbonyloxy group, for example the ethoxycarbonyloxy group. Above all, $Z_o$ represents an etherified hydroxyl group, such as a hydroxyl group etherified with an aliphatic hydrocarbon radical, such as an alkyl or alkenyl radical, for example a lower alkoxy group. It is particularly advantageous to start from starting materials in which $Z_o$ and $R_x$ denote hydroxyl groups etherified with an aliphatic hydrocarbon radical and $Z_o$ has the same meaning as $R_x$, and especially those wherein $R_1$ represents hydrogen, or their tautomers.

The intramolecular condensation is carried out in the usual manner, preferably by heating, in the presence or absence of solvents such as, for example, diphenyl ether, mineral oil or the like, optionally in the presence of condensation agents such as, for example, polyphosphoric acid, aluminum chloride or zinc chloride and/or optionally under a nitrogen atmosphere and/or in a closed vessel under pressure.

Particularly good yields are obtained if the condensation is carried out with a lower alkyl ester of phosphoric acid, for example an ethyl ester, preferably in an inert solvent, for example xylene, at elevated temperatures of about 140°–150°.

The new compounds can also be obtained if, in a compound of the formula V

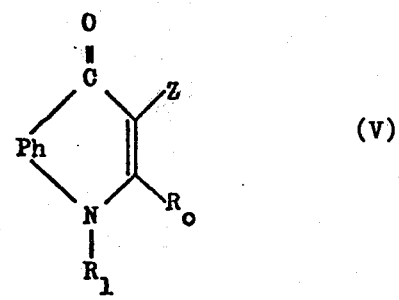

(V)

wherein Z denotes a radical which can be converted into a radical of the formula $COR_x$, and Ph, $R_o$, $R_x$ and $R_1$ have the indicated meanings, or in a tautomer of such a compound in which $R_1$ denotes a hydrogen atom, the radical Z is converted into a group of the formula $COR_x$.

A radical Z is above all a group which can be converted by hydrolysis or corresponding alcoholysis or aminolysis into a radical of the formula $COR_x$, such as a functionally modified carboxyl group, with the exception of an esterified and amidised carboxyl group. Such groups are, for example, trihalogenomethyl groups, such as trichloromethyl or tribromomethyl groups, nitrile groups, halogenocarbonyl groups, such as chlorocarbonyl groups, or acid anhydride groupings, for example one of the abovementioned acyloxycarbonyl groupings, or mercaptocarbonyl groups, such as free or substituted, especially alkylated or aralkylated, mercaptocarbonyl groups.

The hydrolysis of the hydrolysable groups, that is to say, for example, of a nitrile group or of an acid halide or acid anhydride radical or of a trihalogenomethyl group, for example of the trichloromethyl group, is carried out in the usual manner, for example with alkaline agents, such as dilute aqueous alkalis, for example sodium hydroxide, or, in particular, with acid agents, for example dilute mineral acids, such as sulphuric acid or hydrochloric acid, preferably at elevated temperature.

If desired, the hydrolysis of the nitrile group can be taken only as far as the formation of the carbamoyl group. The hydrolysis is in that case suitably carried out with, for example, 96% strength sulphuric acid or weakly alkaline hydrogen peroxide, such as with sodium carbonate.

The alcoholysis of the alcoholisable groups is carried out in the usual manner, for example by reaction with the alcohol in question. A nitrile is suitably alcoholysed in the presence of alkaline agents, such as an alkali metal salt, for example a sodium salt, of the alcohol, or preferably in the presence of acid agents, for example hydrochloric acid or sulphuric acid, advantageously in the presence of ammonium chloride.

If an acid halide is used as the starting material, the reaction is suitably carried out in the presence of basic, inorganic or organic, agents, for example alkali metal acetates or alkali metal carbonates, such as sodium acetate or potassium carbonate, or tertiary amines, for example pyridine. Advantageously, catalytic amounts of an acid, for example of one of the acids mentioned, above all sulphuric acid, are added for the alcoholysis of anhydrides.

The aminolysis of the aminolysable groups is carried out in the usual manner, for example by reaction with an amine of the formula $HR_x$, wherein $R_x$ denotes a free amino group or an amino group which is substituted as indicated. Thus, for example, an acid anhydride or an acid halide can be reacted with ammonia or with a corresponding primary or secondary amine, optionally in the presence of basic, organic or inorganic, condensation agents, such as alkali metal carbonates, for example sodium carbonate or potassium carbonate, or tertiary amines, such as pyridine.

The radical Z in the formula V can, however, also represent the group $-COCH_3$, in which case $R_o$ preferably represents hydrogen. The conversion of the group $-COCH_3$ into the carboxyl group $-COOH$ is carried out in the usual manner, especially by the action of hypohalites, for example sodium hypohalites, such as sodium hypochlorite, sodium hypobromite or sodium hypoiodite, or of halogens, such as chlorine, bromine or iodine in an alkaline medium. The reaction is preferably carried out at room temperature or a lowered temperature. The reaction medium used preferentially is a mixture of water and inert organic solvent, such as, for example, cyclic or open-chain ethers.

A further procedure for the manufacture of the new compounds is the intramolecular condensation of a compound of the formula VI

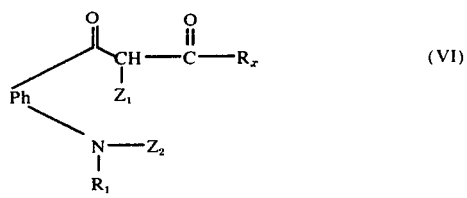

wherein Ph and $R_1$ have the indicated meanings and $R_x$ above all denotes an etherified hydroxyl group or an amino group and one of the radicals $Z_1$ and $Z_2$ represents the

group and the other represents hydrogen, with the radical A representing hydrogen, lower alkyl, an etherified hydroxyl group, a halogen atom or an azido group or forming, together with the carbonyl group, an anhydride or imide group, or, if $Z_1$ and $R_1$ represent hydrogen, the group $-NR_1Z_1$ can represent the isocyanato group.

Lower alkyl groups are the radicals mentioned above for $R_o$.

Etherified hydroxyl groups are above all hydroxyl groups etherified by lower alkyl, lower alkenyl or phenyl-lower alkyl, with lower alkyl, lower alkenyl and phenyl-lower alkyl preferably having the abovementioned meanings.

Halogen is fluorine, bromine, iodine or, above all, chlorine.

Anhydride groups and imide groups are preferably mixed anhydride groups and imide groups with the part A⁻ lost during the cyclisation preferably being a lower alkylcarboxylate anion or a lower alkanoic acid amide anion.

The intramolecular condensation is carried out in the usual manner, preferably in a solvent. In the case that A represents a hydrogen atom or a lower alkyl group, the reaction is carried out, for example, in an anhydrous solvent and advantageously in the presence of a dehydrating agent, such as, for example, a basic dehydrating agent, such as an alkali metal alcoholate. In the case that A has the other meanings mentioned, the intramolecular condensation is preferably carried out in a solvent and in the presence or absence of a basic condensation agent. Suitable solvents are, above all, lower alkanols, such as methanol and ethanol, and also dimethylsulphoxide, dimethylformamide, diphenyl ether or high-boiling hydrocarbons, such as xylenes. Basic condensation agents are, above all, alkali metal alcoholates, such as alkali metal lower alkanolates, for example sodium methylate, sodium ethylate and/or sodium tert.-butylate, or alkali metal hydrides, such as, for example, sodium hydride. The cyclisation reaction is preferably carried out at an elevated temperature, for example at the reflux temperature and, if appropriate, under a nitrogen atmosphere and/or in a closed vessel under pressure.

Compounds of the formula I, wherein $R_o$ denotes hydroxyl and Ph and $R_1$ have the indicated meanings and $R_x$ represents an etherified hydroxyl group, or their tautomeric form of the formula III, can be obtained when, for example, compounds of the formula VIII

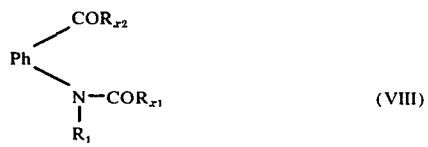

wherein one of the radicals $R_{x1}$ and $R_{x2}$ is an etherified hydroxyl group and the other denotes a group of the formula $-CH_2-COR_x$, and $R_1$, Ph and $R_x$ have the above meanings, are cyclised.

An etherified hydroxyl group is, in particular, an alkoxy group, wherein the alkyl part preferably has up to 8 C atoms and can be straight-chain or branched.

The cyclisation reaction is preferably carried out in a polar solvent and in the presence of a basic condensation agent. Suitable polar solvents are, above all, lower alkanols, such as methanol and ethanol. Basic condensation agents are, above all, alkali metal alcoholates, such as alkali metal lower alkanolates, for example sodium methylate, sodium ethylate and sodium ter.-butylate.

The cyclisation reaction is preferably carried out at an elevated temperature, for example at the reflux temperature, and, if appropriate, under a nitrogen atmosphere and/or in a closed vessel under pressure.

The new compounds of the formula I can furthermore also be obtained if, in a compound of the formula IX

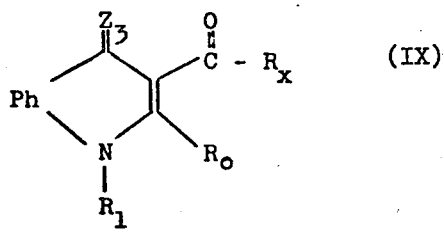

wherein $R_o$, $R_x$, $R_1$ and Ph have the indicated meanings and $Z_3$ represents a functionally modified oxo group or a thioxo group, or in a tautomer of such a compound, wherein $Z_3$ represents a reactive, esterified hydroxyl group or a mercapto group if $R_1$ represents hydrogen and/or $R_o$ represents hydroxyl, or in a salt of such a compound, the group $Z_3$ is converted into the oxo or hydroxyl group by hydrolysis.

A functionally modified oxo group is, for example, an imino group or a ketal grouping, for example a ketal grouping with a lower alkylenediol. A reactive esterified hydroxyl group is, for example, a halogen atom, especially a chlorine atom or bromine atom.

The hydrolysis of $Z_3$ to give the oxo or hydroxyl group can be carried out in the usual manner, preferably by warming in an aqueous agent, advantageously in the presence of acid agents, such as aqueous or alcoholic mineral acids and/or carboxylic acids, for example hydrochloric acid and/or acetic acid, or of basic agents, such as strong bases, for example alkali metal hydroxides. If $Z_3$ is a halogen atom and $R_x$ is an etherified hydroxyl group which is to be preserved during the hydrolysis, the reaction is advantageously carried out in the presence of an acid and in the presence of an alcohol, for example in the presence of a mineral acid in alcoholic solution, the alcohol used advantageously being the alcohol of the formula $R_xH$, or in the presence of an organic acid, such as a carboxylic acid, advantageously in the presence of a corresponding alkali metal salt, for example in the presence of acetic acid and sodium acetate. If $Z_3$ is an imino group, the reaction can be carried out in the presence of diazotising agents, such as nitrous acid or its salts. If $Z_3$ is a thioxo group or a mercapto group, the hydrolysis is preferably carried out under basic conditions, for example those mentioned above, and in the presence of an oxidising agent, such as potassium permanganate, lead oxide or mercury oxide.

The starting materials are known or can, if they are new, be manufactured according to methods which are in themselves known.

Suitably, those starting materials are used for carrying out the reaction according to the invention which lead to the initially particularly mentioned groups of end products and especially to the end products which have been singled out particularly.

Compounds of the formula IV can be obtained, for example, if a compound of the formula IVa

wherein Ph and $R_1$ have the above meanings, is reacted with a compound of the formula IVb

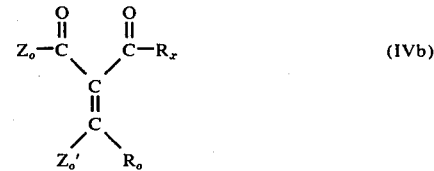

wherein $Z_o$ and $R_x$ have the above meanings and preferably represent an etherified hydroxyl group, $R_o$ has the above meanings and preferably represents hydrogen or lower alkyl and $Z_o'$ denotes a removable group, and above all represents a lower alkoxy group.

Compounds of the formula V, wherein Z represents the $-COCH_3$ group, can be obtained, for example, by cyclisng, in the usual manner, a compound of the formula Va

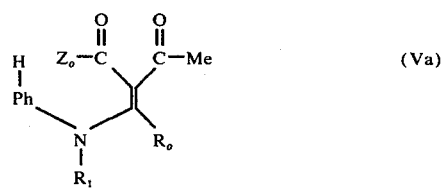

wherein Ph and $R_1$ have the above meanings and $Z_o$ has the above meanings and preferably denotes an etherified hydroxyl group.

Compounds of the formula VIII can be obtained, for example, if a compound of the formula VIIIa

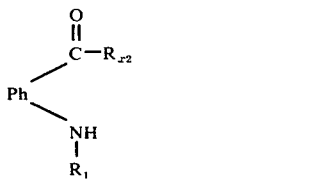
(VIIIa)

wherein Ph, $R_1$ and $R_{x2}$ have the above meanings, is reacted, in the usual manner, with a compound of the formula VIIIb

(VIIIb)

wherein $R_x$ has the above meanings and $R_x''$ denotes a removable group and preferably represents halogen, such as, for example, chlorine.

Compounds of the formula IX, wherein $Z_3$ denotes a chlorine atom, can be manufactured, for example, by cyclising a compound of the formula IXa

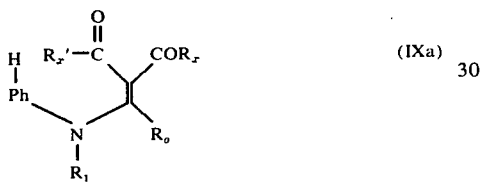
(IXa)

wherein Ph has the above meanings, $R_x$ represents an etherified hydroxyl group or an amino group, $R_x'$ preferably is an etherified hydroxyl group, $R_1$ is hydrogen if $R_o$ is not hydroxyl, or has the remaining meanings indicated above, and $R_o$ is hydroxyl if $R_1$ is not hydrogen or has the remaining meanings indicated above, in the presence of, for example, phosphoryl chloride, in the usual manner.

Starting materials of the formula IX, wherein $R_1$, $R_o$, $R_x$ and Ph have the above meanings and $Z_3$ represents a thioxo group, or, if $R_1$ denotes hydrogen and/or $R_o$ denotes hydroxyl, represents a mercapto group, their salts, and processes for their manufacture, also form a subject of the invention.

The invention thus relates to compounds of the formula X

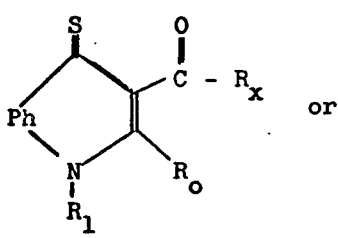
or

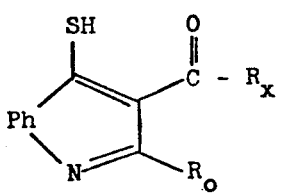
or

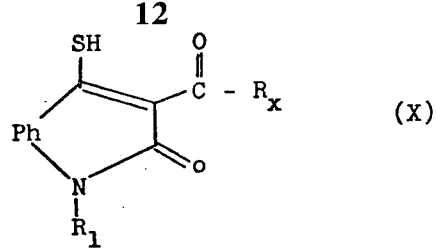
(X)

wherein Ph, $R_1$, $R_o$ and $R_x$ have the above meanings.

The new compounds of the formula X possess valuable pharmacological properties such as, in particular, the properties mentioned earlier for compounds of the formula I. However, the new compounds are also valuable intermediate products for the manufacture of other useful materials, especially of pharmacologically active compounds. Compounds to be particularly singled out are those of the formula Xa

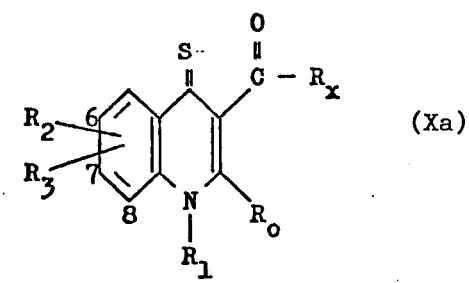
(Xa)

or of its tautomeric form, wherein $R_o$, $R_1$ and $R_x$ have the abovementioned meanings, $R_2$ occupies positions 6, 7 or 8 and represents a cycloalkyl or cycloalkenyl radical with 5–8 ring members which can also be substituted by lower alkyl, lower alkoxy, oxo groups, hydroxyl groups or lower alkanoyl groups, or represents the 1-adamantyl radical, and $R_3$ occupies any desired free position of the 1,2-phenylene radical and denotes lower alkyl, lower alkoxy or above all halogen or hydrogen.

Compounds to be singled out particularly are those of the formula Xa or of its tautomeric form, wherein $R_2$, $R_3$ and $R_1$ have the above meanings and $R_o$ represents hydrogen, lower alkyl with up to 4 C atoms, hydroxyl or lower alkoxy and $R_x$ denotes hydroxyl, lower alkoxy or an optionally substituted amino group.

Compounds to be singled out above all are those of the formula Xa or of its tautomeric form, wherein $R_2$ occupies positions 6, 7 or 8 of the quinoline skeleton and denotes cycloalkyl with 5 to 8 ring members, cycloalkenyl with 5–7 ring members or 1-adamantyl, $R_3$ occupies any desired free position of the 1,2-phenylene radical and represents hydrogen, lower alkyl, lower alkoxy or halogen, $R_1$ denotes hydrogen, lower alkyl, lower alkenyl or aryl-lower alkyl, $R_o$ represents hydrogen, lower alkoxy or hydroxyl and $R_x$ denotes hydroxyl or lower alkoxy or an optionally substituted amino group.

Compounds to be singled out very particularly are those of the formula Xa or of its tautomeric form, wherein $R_2$ occupies positions 6, 7 or 8 of the quinoline skeleton and denotes cycloalkyl with 5 to 8 ring members, cycloalkenyl with 5–8 ring members or 1-adamantyl, $R_3$ can occupy one of the free positions of the 1,2-phenylene radical and represents hydrogen, halogen or lower alkoxy with up to 4 C atoms, $R_1$ denotes hydrogen, lower alkyl with up to 6 C atoms, lower alkenyl with 3–4 C atoms or aryl-lower alkyl with up to 3 C atoms in the lower alkyl part, $R_o$ represents hydrogen or hydroxyl and $R_x$ denotes hydroxyl, lower alkoxy with 1-3 C atoms or optionally substituted anilino, and in particular $R_2$ is cyclopentyl, cyclohexyl, cycloheptyl, cyclohexen-1-yl, cyclooctyl or 1-adamantyl, $R_3$ is hydrogen, chlorine or methoxy, $R_1$ represents hydrogen, methyl, ethyl, hexyl, allyl or benzyl, $R_o$ is hydrogen or hydroxyl and $R_x$ represents hydroxyl, methoxy, ethoxy or p-chloroanilino.

The new compounds of the formula X can be obtained according to methods which are in themselves known.

Thus, for example, the new compounds can be obtained by converting the group —SY into the group —SH in a compound of the formula XI

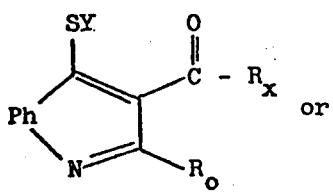

or

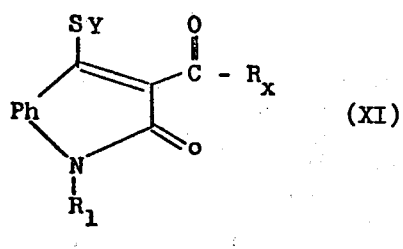

(XI)

wherein Ph, $R_1$, $R_o$ and $R_x$ have the above meanings and the group —SY denotes a group which can be converted into the mercapto group —SH.

A group —SY which can be converted into the group —SH is, for example, an amidinothio group of the formula

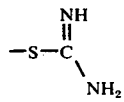

or a group of the formula

wherein R preferably represents ($C_{1-7}$)-lower alkyl or phenyl-($C_{1-4}$)-lower alkyl.

The conversion of the group —SY into the mercapto group —SH is preferably effected by hydrolysis.

An amidinothio group is preferably hydrolysed in a strongly basic medium. Suitable reaction media for this purpose are, in particular, aqueous solutions of alkali metal hydroxides, such as sodium hydroxide or potassium hydroxide, and also aqueous solutions of ammonia. The reaction is preferably carried out at room temperature or elevated temperature. A thioester group or a dithioester group is converted into the mercapto group in the usual manner. The hydrolysis is preferably carried out in the presence of bases, such as an alkali metal hydroxide, for example sodium hydroxide or potassium hydroxide, or an alkali metal carbonate, for example sodium carbonate or potassium carbonate. The hydrolysis can, however, also be carried out with strong acids, for example a strong mineral acid, such as a hydrogen halide acid, for example hydrochloric acid or sulphuric acid. The reaction is preferably carried out at room temperature or elevated temperature. When using compounds of the formula XI, wherein the —$COR_x$ group represents an esterified carboxyl group, care must be taken that the —$COR_x$ group should remain preserved during the hydrolysis.

The new compounds can furthermore be obtained by converting the group $Y_1$ into the mercapto group —SH in a compound of the formula XII

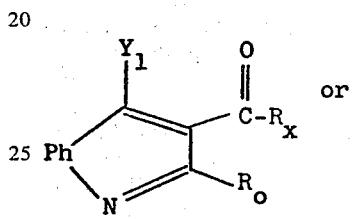

or

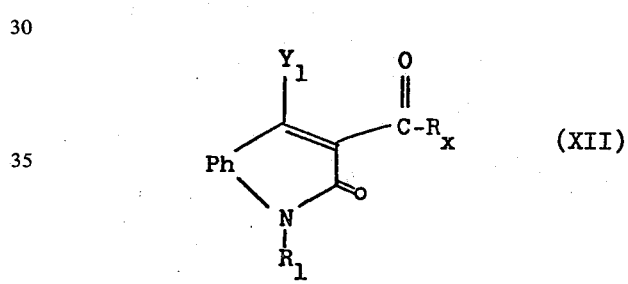

(XII)

wherein $Y_1$ is a nucleophilically removable group and $R_1$, $R_o$, $R_x$ and Ph have the above meanings.

A nucleophilically removable group $Y_1$ is preferably a halogen atom, such as, for example, a chlorine, iodine or, especially, bromine atom, or an ammonium group, such as a tri-lower alkylammonium group, for example the trimethylammonium group, or a lower alkylsulphonyl group, for example the methylsulphonyl group.

The conversion of the group —$Y_1$ into the mercapto group is preferably effected with an alkali metal sulphide, such as sodium sulphide or potassium sulphide, or above all with an alkali metal bisulphide, such as sodium bisulphide or potassium bisulphide.

The reaction is preferably carried out in an aqueous medium or in a mixed aqueous/organic solvent. Suitable organic solvents are, in particular, polar solvents, such as lower alkanols, for example methanol or ethanol. The reaction is carried out at room temperature or preferably at elevated temperature and optionally under elevated pressure. It is advantageous to allow a stream of hydrogen sulphide to bubble through the reaction medium during the reaction.

Compounds of the formula X, wherein $R_x$ and Ph have the above meanings, $R_1$ has the above meanings with the exception of hydrogen and $R_o$ has the above meanings with the exception of hydroxyl, can also be manufactured by converting the keto group >C=$O_1$ into the thioketo group >C=S in a compound of the formula XIII

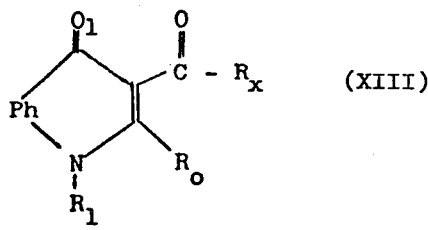

wherein $R_x$ and Ph have the above meanings and $R_1$ has the above meanings with the exception of hydrogen and $R_o$ has the above meanings with the exception of hydroxyl.

The reaction takes place in the usual manner. Suitable sulphiding agents are, for example, phosphorus sulphides, such as, especially, phosphorus pentasulphide. The reaction can be carried out in the presence or the absence of solvents. Examples of suitable solvents are high-boiling hydrocarbons such as, for example, toluene. The reaction is preferably carried out at an elevated temperature. In the reaction, care must be taken that the keto group in the $-CO-R_x$ group should not also be converted to the thioketo group.

The starting materials which lead to the compounds according to the invention, of the formula X, are known or can, if they are new, be manufactured according to methods which are in themselves known.

Compounds of the formula XI, wherein the $-SY$ group represents an amidinothio group can be manufactured, for example, by reacting a compound of the formula XII with thiourea.

Suitably, those starting materials are used for carrying out the reaction according to the invention which lead to the initially particularly mentioned groups of end products and especially to the end products which have been singled out particularly.

In resulting compounds of the formula I or X substituents can be introduced, modified or removed, within the scope of the end products.

Thus, it is possible, in resulting compounds of the formula I or X, wherein $R_1$ denotes a hydrogen atom, to introduce an aliphatic or cycloaliphatic hydrocarbon radical, an araliphatic radical or a lower hydroxyalkyl radical. This introduction is carried out in the usual manner, for example by reaction with a reactive ester of a corresponding alcohol or, if appropriate, with a corresponding epoxide. Reactive esters which can be used for this purpose are above all esters with strong inorganic or organic acids, for example with hydrogen halide acids, such as hydrochloric acid, hydrobromic acid or hydriodic acid, with sulphuric acid, or with organic sulphonic acids, for example arylsulphonic acids, such as p-toluenesulphonic acids, p-bromobenzenesulphonic acid or benezenesulphonic acid.

The reaction is carried out in the usual manner. Preferably, the compound to be substituted is employed in the form of a metal salt, such as an alkali metal salt, or the reaction is carried out in the presence of basic condensation agents which are able to form the said metal salts, for example amides, hydrides, hydrocarbon compounds, hydroxides or alcoholates of alkali metals, such as lithium, sodium or potassium. If the radical $R_1$ is introduced into a compound in which $COR_x$ is an esterified carboxyl group, the reaction is advantageously carried out under mild conditions, such as a lower temperature and/or in a more weakly basic medium, for example in the presence of alkali metal carbonates, such as, for example, potassium carbonate, if it is desired to avoid the hydrolysis of this esterified carboxyl group.

Furthermore it is possible in resulting compounds to convert, for example, free carboxyl groups, esterified carboxyl groups and amidised carboxyl groups into one another.

Thus, resulting compounds in which $R_x$ denotes a free hydroxyl group, can be esterified. The esterification is carried out in the usual manner, for example by reaction with a corresponding alcohol of the formula $R_xH$, wherein $R_x$ denotes an etherified hydroxyl group, optionally in the presence of a suitable catalyst. Advantageously, the free acid is reacted with the corresponding alcohol in the presence of an acid, such as a mineral acid, for example sulphuric acid or hydrochloric acid. However, the esterification can also be carried out by reaction with a corresponding diazo compound, such as, for example, a diazoalkane.

Free or esterified carboxyl groups

can be converted into amidised carboxyl groups in the usual manner, for example by reaction with ammonia or corresponding amines which possess at least one hydrogen atom on the nitrogen atom, with dehydration of the ammonium salt produced as an intermediate, if necessary.

Free carboxyl groups can, for example, also be converted into acid halide or acid anhydride groupings in the usual manner, for example by reaction with halides of phosphorus or sulphur, such as thionyl chloride, phosphorus pentachloride or phosphorus tribromide, or with acid halides, such as chloroformic acid esters. The acid anhydride or acid halide groups can then be converted into esterified or amidised carboxyl groups in the usual manner by reaction with corresponding alcohols or with ammonia or with corresponding amines possessing at least one hydrogen atom on the nitrogen atom, for example as indicated above.

Resulting compounds in which $R_x$ denotes an etherified hydroxyl group or a free or substituted amino group can be hydrolysed to the free acids in the usual manner. The hydrolysis is carried out in the usual manner, for example in the presence of strong acids or of bases, and preferably in the presence of solvents. If desired, oxidising agents, such as nitrous acid, can be added when hydrolysing carbamyl groups.

The hydrolysis of an esterified carboxyl group to give the free carboxyl group can also be carried out simultaneously with the introduction of a radical $R_1$, for example by introducing $R_1$ in a strongly basic medium.

The oxo, hydroxyl, acyloxy, lower alkoxy and lower alkenyloxy groups which can be present on the cycloaliphatic radical of the radical Ph can be converted into one another.

For example, hydroxyl groups can be alkylated or alkenylated or acylated. This can be done, for example, by reaction with a reactive ester, for example one of those mentioned above, of a lower alkanol or alkenol.

The acylation is carried out in the usual manner, for example using carboxylic acids or, advantageously, their reactive derivatives, such as halides, especially chlorides, or anhydrides, suitably in the presence of acid agents or above all of basic agents, for example sulphuric acid or an inorganic or organic base, for example sodium hydroxide or pyridine.

Acyloxy groups can be converted into free hydroxyl groups in the usual manner, for example by hydrolysis, for example in the presence of strong acids or of bases.

Furthermore, oxo groups can be reduced to hydroxyl groups, for example catalytically, for example as indicated above, with sodium in a lower alkanol, for example ethanol, with a di-light metal hydride, for example sodium borohydride, or by the Meerwein-Ponndorf method with an alcohol in the presence of an aluminum alcoholate. However, the oxo oxygen can also be replaced by two hydrogen atoms, for example by the Wolff-Kishner or Huang-Minlon method by decomposing the hydrazone, by the Clemmensen method with zinc and hydrochloric acid or by reduction of the thioketal, for example with Raney nickel.

Hydroxyl groups can be oxidised to oxo groups, for example with chromic acid or by the Oppenauer method with a ketone in the presence of an aluminium alcoholate.

Hydroxyl groups, lower alkoxy groups, lower alkenyloxy groups and acyloxy groups can also be split off with formation of a double bond, advantageously in the presence of acid agents.

In resulting compounds which contain unsaturated radicals, for example unsaturated cycloaliphatic radicals or alkenyl radicals, the double bonds can be hydrogenated. The hydrogenation is carried out in the usual manner, above all with catalytically activated hydrogen, for example in the presence of Raney nickel or noble metal catalysts, such as platinum or palladium, optionally in the form of their oxides, and suitably in an inert solvent, for example an alkanol or dioxane, optionally under pressure, or with nascent hydrogen, for example with sodium and alcohol.

In resulting compounds which contain nitro groups, these groups can be reduced to amino groups, for example with iron and hydrochloric acid, or catalytically, for example as indicated above.

New compounds in which $R_o$ denotes a lower alkoxy group can be manufactured from the same compounds in which $R_o$ denotes a hydroxyl group, by alkylation with one of the abovementioned reactive esters of a lower alcohol and one of the abovementioned basic condensation agents.

Depending on the process conditions and starting materials, acid end products, for example those in which $R_x$ denotes a free hydroxyl group, are obtained in the free form or in the form of their salts with bases. Resulting free acid compounds can be converted in the usual manner, for example by reaction with corresponding basic agents, into the salts with bases, above all into therapeutically usable salts with bases, for example salts with organic amines or metal salts. Possible metal salts are above all alkali metal salts or alkaline earth metal salts, such as sodium, potassium, magnesium or calcium salts. Free acids can be liberated from the salts in the usual manner, for example by reaction with acid agents. The salts can also be used for purifying the new compounds, for example by converting the free compounds into their salts, isolating these and reconverting them to the free compounds. Because of the close relationships between the new compounds in the free form and in the form of their salts, the free compounds are where appropriate also to be understood, in the preceding and following text, to include the corresponding salts, in respect of general sense and intended use.

Depending on the choice of the starting materials and procedures, the new compounds which contain an asymmetrical carbon atom can be in the form of optical antipodes or racemates or, in cases where they contain more than one asymmetrical carbon atom, of racemate mixtures.

Racemate mixtures can be separated into the two stereoisomeric (diastereomeric) pure racemates on the basis of the physico-chemical differences of the constituents, in a known manner, for example by chromatography and/or fractional crystallisation.

Pure racemates can also be resolved into the diastereomers according to known methods, for example by recrystallisation from an optically active solvent, with the aid of micro-organisms or, for example, in the case of the acids, by reaction with an optically active base which forms salts with the racemic compound and separation of the salts obtained in this manner, for example on the basis of their different solubilities, and the antipodes can be liberated from the diastereomers by the action of suitable agents, such as acids. Advantageously, the more active of the two antipodes is isolated.

The invention also relates to those embodiments of the process according to which a compound obtainable as an intermediate at any stage of the process is used as the starting material and the missing process steps are carried out or the process is discontinued at any stage, or a starting material is formed under the reaction conditions, or a reactant is present, if relevant, in the form of a salt, and/or racemate and/or antipode.

The new compounds can be used, for example, in the form of pharmaceutical preparations in which they are present in the free form or, if appropriate, in the form of their non-toxic salts, mixed with a pharmaceutical, organic or inorganic, solid or liquid excipient which is suitable, for example, for topical, enteral, for example oral, or parental administration. Suitable materials for forming the excipient are those which do not react with the new compounds, such as, for example, water, gelatine, lactose, starch, stearyl alcohol, magnesium stearate, talc, vegetable oils, benzyl alcohols, rubber, propylene glycols, white petroleum jelly or other known medicinal excipients. The pharmaceutical preparations can be, for example, in the form of tablets, dragées, capsules, ointments, creams, pastes or suppositories or in a liquid form as solutions (for example as an elixir), suspensions or emulsions. They are optionally sterilised and/or contain auxiliaries, such as preservatives, stabilisers, wetting agents or emulsifiers, solubilising agents and salts for regulating the osmotic pressure, or buffers. They are manufactured in a manner which is in itself known and contain from about 0.1% to about 90%, especially from about 1% to about 50%, of the active material; they can, if desired, contain additional physiologically active materials.

The new compounds can also be used in veterinary medicine, for example in one of the abovementioned forms or in the form of feeding stuffs or of additives to animal fodder.

The antimicrobial properties mentioned show that the new compounds can be used not only in human and veterinary medicine but can also find further application in hygiene and cosmetics and the protection of materials. In addition to their use in systemic infections, the new compounds can also be used for the treatment of diseases of the skin of warm blooded animals, caused by bacteria and fungi, and for the disinfection of the mouth, throat and intestine. They are preferably used in the form of pharmaceutical or cosmetic compositions which consist of about 0.1 to 5% of a compound of the present invention or of one of its pharmaceutical or cosmetically acceptable salts and the customary pharmaceutical or cosmetic excipients. For external use, for example for the disinfection of healthy skin and for the disinfection of wounds and for the treatment of dermatoses and affections of the mucous membrane, caused by bacteria or fungi, it is in particular possible to use ointments, powders, tinctures and sprays.

Ointment bases can be anhydrous for example consist of mixtures of lanoline and white petroleum jelly, or can be aqueous emulsions in which the active compound is suspended. Suitable excipients for powders are, for example, starches, such as rice starch, of which the specific gravity can, if desired, be reduced, for example by adding highly disperse silica, or be increased, for example by adding talc, Tinctures contain at least one compound of the formula I or X or of one of its pharmaceutically or cosmetically acceptable salts in aqueous ethanol, in particular 45–75% strength ethanol, to which 10–20% of glycerol are added if appropriate. Particularly for the disinfection of healthy skin it is also possible to use solutions which have been prepared with the aid of customary solubilising agents such as, for example, ethylene glycol, and, optionally, of emulsifiers.

Suitable preparations for disinfection of the mouth and throat are, on the one hand, gargles, or concentrates for the preparation thereof, especially alcoholic solutions containing approx. 1–5% of active compound, to which glycerol and/or aroma substances can have been added, and, on the other hand, lozenges, that is to say solid unit dosage forms having a relatively high content of sugar or similar materials and an active substance content of approx. 0.2–20%, together with the customary additives, such as binders and aroma substances.

For disinfection of the intestinal and urinary tract it is in particular possible to use solid unit dosage forms, such as tablets, dragées and capsules, which preferably contain between 10% and 90% of a compound of the formula I or of the formula X or one of its pharmaceutically acceptable salts, in order to permit the administration of daily doses of between 0.1 and 2.5 g to human adults or of suitably reduced doses to children. To prepare tablets and dragée cores, the new compounds are combined with solid, pulverulent excipients, such as lactose, sucrose, sorbitol, maize starch, potato starch or amylopectin, cellulose derivatives of gelatine, preferably with addition of lubricants, such as magnesium stearate, calcium stearate or polyethylene glycols of suitable molecular weight. Dragée cores are subsequently coated, for example with concentrated sugar solutions which can, for example, additionally contain gum arabic, talc and/or titanium dioxide, or with a lacquer dissolved in readily volatile organic solvents or solvent mixtures. Dyestuffs can be added to these coatings, for example to characterise various doses of active compound. Beads (bead-shaped sealed capsules) and other sealed capsules consist, for example, of a mixture of gelatine and glycerine, and contain, for example, mixtures of a compound of the formula I or of the formula X or of one of its salts, with polyethylene glycol. Push-fit capsules contain, for example, granules of an active substance mixed with solid, pulverulent excipients, such as, for example, lactose, sucrose, sorbitol, mannitol, starches, such as potato starch or maize starch, or amylopectin, cellulose derivatives or gelatine, as well as magnesium stearate or stearic acid.

The compounds of the formula I or of the formula X which can be manufactured according to the invention, and their salts, can be used in very diverse ways for protecting organic materials or articles against attack by microorganisms especially by bacteria and fungi. Thus, the compounds can be incorporated directly into the material to be protected, for example into material based on synthetic resins, such as polyamides and polyvinyl chloride, into paper treatment liquors, into print thickeners made of starch or cellulose derivatives, into lacquers and paints which contain, for example, casein, into cellulose, into viscose spinning composition, into paper, into animal mucins or oils, into permanent coatings based on polyvinyl alcohol, into cosmetic articles, such as into soaps, for example into hand soaps or toilet soaps, into ointments or into powders. Further, they can also be added to preparations of inorganic or organic pigments for use by painters, or to plasticisers and the like.

Compounds of the formula I or of the formula X can also be used in the form of their organic solutions, for example as so-called "sprays", as dry-cleaning agents or for the impregnation of timber, possible organic solvents being, preferably, water-immiscible solvents, especially petroleum fractions, but also water-miscible solvents, such as lower alcohols, for example methanol or ethanol or ethylene glycol monomethyl ether or ethylene glycol monoethyl ether.

The compounds can also be used, together with wetting agents or dispersing agents, in the form of their aqueous dispersions, for example for protecting substances which tend to rot, such as for protecting leather, paper and the like.

Active substance solutions or dispersions which can be used to protect these materials advantageously contain at least 0.001 g of active substance/liter.

A further field of use of the new compounds is the disinfection of laundry and the protection of laundry against attack by micro-organisms. For this purpose, either washing liquors or rinsing liquors are used, which contain the said compounds, advantageously in concentrations of approx. 1–200 $\mu$g/ml, relative to the liquor.

As detergent substances the wash liquors contain, for example, anionic compounds, such as aromatic sulphonic acids substituted by lipophilic groups, or their water-soluble salts, say the sodium salt of dodecylbenzenesulphonic acid, or water-soluble salts of sulphuric acid monoesters of higher-molecular alcohols or of their polyglycol ethers, for example soluble salts of dodecyl alcohol-sulphate or of dodecyl alcohol-polyglycol ether sulphate, or alkali metal salts of higher fatty acids (soaps), or non-ionic detergent substances, such as polyglycol ethers of higher fatty alcohols, or polyglycol ethers of higher-molecular alkylated phenols, as well as so-called "amphoteric" detergent substances, say reaction products of the alkali metal salts of lower halogeno-fatty acids with polyalkylenepolyamines containing lipophilic radicals, for example with lauryl-diethylenetriamine. In addition, the liquor can also contain customary auxiliaries, such as water-soluble perborates, polyphosphates, carbonates, silicates, optical brighteners, plasticisers, salts which have an acid reaction, such as ammonium fluosilicate or zinc fluosilicate, or certain organic acids, such as oxalic acid, and also finishing agents, for example based on synthethic resins or starch.

Laundry which can be sterilised with washing liquors or rinsing liquors containing compounds according to the invention is above all organic fibre material, expecially material of natural origin, such as cellulosic material, for example cotton, or materials containing polypeptide, for example wool or silk, or fibre material of synthetic origin, such as material based on polyamide, polyacrylonitrile or polyester, or mixtures of the above-mentioned fibres.

The new compounds which can be manufactured according to the invention, when used in the above-mentioned concentrations, impart extensive and long-lasting freedom from germs both to the liquor and to the laundry treated therewith.

The new compounds which can be manufactured according to the invention are also very active against the bacterial flora which causes perspiration odour. Because of their low topical toxicity they are therefore also suitable for use as deodorants for laundry, for example when incorporated into cleaning agents, such as into soaps, or in shampoos, or as additives to cosmetics, such as ointments or creams.

In all forms in which they are used, whether intended for industrial, cosmetic, hygienic or medical fields of application, the new compounds can be present as the sole active substances or be combined with other known antimicrobial, expecially anti-bacterial and/or anti-mycotic, active substances, for example in order to broaden the action spectrum. For example, they can be combined with halogenated salicylic acid alkylamides and anilides, with halogenated diphenylureas, with halogenated benzoxazoles or benzoxazolones, with polychlorohydroxydiphenylmethanes, polychlorohydroxydiphenyl ethers or halogenodihydroxydiphenyl sulphides, with bactericidal 2-imino-imidazolidines or -tetrahydropyrimidines, with bactericidal quaternary compounds, with certain dithiocarbamic acid derivatives, such as with tetramethylthiuram sulphide, with substituted o-phenoxyphenyl esters, for example 2-acetoxy-4, 4′-dichlorodiphenyl ether or 2-acetoxy-4, 2, 4′-trichlorodiphenyl ether, or with phenyl-3-iodo-2-propynyl ether or halogen-substituted derivatives thereof, for example 2, 3-dichlorophenyl- or 2, 4, 5-trichlorophenyl-3-iodo-2-propynyl ether. If appropriate, excipients with pharmacologically advantageous inherent properties, such as, for example, sulphur as a powder base or zinc stearate as a component of ointment bases, can also be used.

The daily dose is about 30–100 mg administered orally in the case of a warm-blooded animal of about 75 kg body weight.

The examples which follow explain in more detail the manufacture of the new compounds and of the corresponding starting materials and intermediate products and describe some typical use forms for various fields of application.

However, the examples are not to be regarded as limiting the invention.

EXAMPLE 1

A solution of 58 g of (4-cyclohexyl-anilino)-methylene-malonic acid diethyl ester in 150 ml of diphenyl ether is boiled for 15 minutes under reflux. It is cooled to 25°C and ether is added. The crystals which have separated out are filtered off and recrystallised from ethanol, whereupon 3-carboethoxy-4-hydroxy-6-cyclohexyl-quinoline is obtained in the form of pale brown crystals of melting point 275°–277°C (decomposition).

4-(Cyclohexyl-anilino)-methylenemalonic acid diethyl ester, used as the starting material, can be prepared as follows:

A mixture of 30 g of 4-cyclohexyl-aniline and 37.5 g of ethoxymethylenemalonic acid diethyl ester is heated for 30 minutes to 130°C whilst distilling off the ethanol which forms. The (4-cyclohexyl-anilino)-methylenemalonic acid diethyl ester thus obtained is a viscous oil can be used directly for the cyclisation described above.

EXAMPLE 2

A solution of 11 g of 3-carboethoxy-4-hydroxy-6-cyclohexyl-quinoline in 300 ml of ethanol and 50 ml of 10 N sodium hydroxide solution is heated for 3 hours on a water bath. It is then diluted with 200 ml of water and the clear solution is acidified with concentrated hydrochloric acid, whereupon a solid precipitate results. This is filtered off and recrystallised from ethanol or dimethylformamide, and gives 4-hydroxy-6-cyclohexyl-quinoline-3-carboxylic acid in the form of pale yellow crystals of melting point 263°–265°C.

The sodium salt of 4-hydroxy-6-cyclohexyl-quinoline-3-carboxylic acid is obtained by reaction with the calculated amount of sodium hydroxide solution.

EXAMPLE 3

70 ml of ethyl iodide is added with stirring to a suspension of 13 g of 3-carboethoxy-4-hydroxy-6-cyclohexyl-guinoline in 200 ml of ethanol and 200 ml of 2 N sodium hydroxide solution and the mixture is slowly warmed to 60°C, whereupon a clear solution results. After stirring for a further 13 hours at 60°C, the reaction solution is evaporated to half on a rotary evaporator in vacuo. The residue is cooled to room temperature and acidified with 2 N hydrochloric acid, whereupon a white solid precipitate results. This is filtered off, washed with water and dried in vacuo at 100°C. After recrystallisation from methylene chloride/petroleum ether, 1-ethyl-4-oxo-6-cyclohexyl-1,4-dihydro-quinoline-3-carboxylic acid is obtained in the form of white crystals of melting point 168°–169°C (decomposition).

Reaction with the calculated amount of sodium hydroxide solution gives the sodium salt of 1-ethyl-4-oxo-6-cyclohexyl-1,4-dihydro-quinoline-3-carboxylic acid.

EXAMPLE 4

100 g of diphenyl ether are added to 34.8 g of 3-cyclohexylanilino-methylenemalonic acid diethyl ester and the mixture is boiled under reflux for 10 minutes. The hot reaction mixture is cooled to room temperature and thoroughly kneaded with ether, the mixture is cooled to −10°C and the product is filtered off in the cold. The crystalline precipitate is washed with cold ether. For futher purification, tion, the crystals are boiled up in 200 ml of absolute ethanol and filtered off hot. This gives 3-carboethoxy-4-hydroxy-7-cyclohexyl-quinoline of melting point 303°–305°C (evolution of gas).

The starting material can be obtained as follows: 52.5 g of 3-cyclohexylaniline and 66 g of ethoxymethylenemalonic acid diethyl ester are heated to 130°C for 1 hour in a distillation apparatus. The distillation residue contains crude 3-cyclohexylanilino-methylenemalonic acid diethyl ester which can be further processed directly, without additional purification.

EXAMPLE 5

A suspension of 15 g of 3-carboethoxy-4-hydroxy-7-cyclohexyl-quinoline in 150 ml of ethanol and 150 ml of 2 N sodium hydroxide solution is boiled under reflux for 7 hours. It is then evaporated to dryness, the residue is dissolved in ethanol-water and the solution is adjusted to pH value 7 with 2 N hydrochloric acid. The crystalline residue thereby produced is filtered off and thoroughly washed with water. 4-Hydroxy-7-cyclohexylquinoline-3-carboxylic acid thus obtained, melts at 241°–243°C (evolution of gas).

Reaction with the calculated amount of sodium hydroxide solution gives the sodium salt of 4-hydroxy-7-cyclohexylquinoline-3-carboxylic acid.

EXAMPLE 6

A suspension of 32.7 g of 3-carboethoxy-4-hydroxy-7-cyclohexyl-quinoline and 7.1 g of sodium hydride (50% strength in mineral oil) in 400 ml of absolute dimethylformamide is stirred for 45 minutes at room temperature with exclusion of water. In the course thereof, the temperature of the reaction mixture rises to 35°C and a homogeneous solution is produced. 39 g of ethyl iodide are added dropwise to this solution over the course of 10 minutes whilst stirring and the mixture is stirred for a further 2½ hours at 55°C. It is then cooled to room temperature and 500 ml of water are added slowly, whilst stirring. The resulting precipitate is filtered off, well washed with water and recrystallised from ethanol-ether. 1-Ethyl-3-carboethoxy-4-oxo-7-cyclohexyl-1,4-dihydroquinoline, thus obtained, melts at 176°–178°C.

EXAMPLE 7

A suspension of 18.2 g of the ester described in Example 6, in 200 ml of ethanol and 200 ml of 2 N sodium hydroxide solution, is boiled for 15 hours under reflux. The clear solution thereby produced is evaporated to dryness in vacuo. The residue is dissolved in approx. 700 ml of hot water, the solution is adjusted to pH value 1 with 2 N hydrochloric acid and the crystals thereby produced are filtered off and washed with water. 1-Ethyl-4-oxo-7-cyclohexyl-1,4-dihydroquinoline-3-carboxylic acid thus obtained, melts at 222°–224°C. Reaction thereof with the calculated amount of sodium hydroxide solution gives the sodium salt of 1-ethyl-4-oxo-7-cyclohexyl-1,4-dihydroquinoline-3-carboxylic acid.

EXAMPLE 8

Starting from (4-cyclopentyl-anilino)-methylenemalonic acid diethyl ester, 3-carboethoxy-4-hydroxy-6-cyclopentylquinoline can be prepared analogously to the description in Example 1; melting point 285°C (from ether/diphenyl ether).

EXAMPLE 9

Starting from (4-cyclohexyl-3-chloro-anilino)-methylene-malonic acid diethyl ester, 3-carboethoxy-4-hydroxy-6-cyclohexyl-7-chloro-quinoline can be prepared analogously to the description in Example 1; melting point 280°C with decomposition (from ethanol/ether).

EXAMPLE 10

Starting from (4-cycloheptyl-anilino)-methylene-malonic acid diethyl ester, 3-carboethoxy-4-hydroxy-6-cycloheptyl-quinoline can be prepared analogously to the description in Example 1; melting point 275°C (from ether/diphenyl ether).

EXAMPLE 11

Starting from [4-(cyclohexen-1-yl)-anilino]-methylene-malonic acid diethyl ester, 3-carboethoxy-4-hydroxy-6-cyclohexen-1-yl)-quinoline can be prepared analogously to the description in Example 1; melting point 285°–287°C (from ether/diphenyl ether).

The 4-(cyclohexen-1-yl)-aniline required for the manufacture of [4-(cyclohexen-1-yl)-anilino]-methylenemalonic acid diethyl ester can be obtained as follows:

A mixture of 65 g of p-(cyclohexen-1-yl)-acetophenone, 43.5 g of hydroxylamine hydrochloride and 43.5 g of (anhydrous) sodium acetate in 1.2 l of ethanol is heated to 70°C for 15 minutes whilst stirring and 520 ml of water are then added. The clear solution thereby obtained is kept at 70°C for 30 minutes and water is then added until the mixture turns cloudy. On cooling, crude p-(cyclohexen-1-yl)-acetophenoneoxime crystallises and is obtained by filtering the reaction solution; melting point 154°–156°C. 6g of p-toluene-sulphonic acid dissolved in 20 ml of absolute pyridine are added to 5 g of this oxime, dissolved in 20 ml of absolute pyridine, at room temperature, whilst stirring and the mixture is kept for 4 hours at a temperature below 45°C. The mixture is then partitioned between 6 N hydrochloric acid and methylene chloride. The organic phases are washed until neutral, dried over sodium sulphate and evaporated in vacuo. Recrystallisation of the evaporation residue from ethyl acetate/ether gives crude 4-(cyclohexen-1-yl)-acetanilide of melting point 152°C.

A solution of 20 g of this acetanilide and 20.8 g of potassium hydroxide in 4 ml of water and 80 ml of ethylene glycol is heated for 6 hours in a heating bath at 200°C. To obtain a homogeneous solution, small amounts of ethanol are added during warming. The reaction mixture is allowed to cool to room temperature and is partitioned between 3 times 200 ml of ether and 600 ml of water. The organic phases are washed with saturated sodium chloride solution, dried over sodium sulphate and evaporated to dryness in vacuo. The crude oily 4-(cyclohexen-1-yl)-aniline which remains in the residue is used further directly, without additional purification.

EXAMPLE 12

Starting from [4-adamantyl-(1)-anilino]-methylenemalonic acid diethyl ester, 3-carboethoxy-4-hydroxy-6-[adamantyl-(1)]-quinoline can be prepared analogously to the description in Example 1; melting point 300°C.

EXAMPLE 13

Starting from (2-cyclohexyl-anilino)-methylenemalonic acid diethyl ester, 3-carboethoxy-4-hydroxy-8-cyclohexyl-quinoline can be prepared analogously to the description in Example 1; melting point 230°C. (From ether/diphenyl ether).

The compounds of Examples 14–16 can be obtained by reaction of the corresponding 1-unsubstituted esters with a corresponding alkyl halide, alkenyl halide or aralkyl halide in the presence of an alkali metal carbonate such as, for example, potassium carbonate.

EXAMPLE 14

Starting from 3-carboethoxy-4-hydroxy-6-cyclohexyl-7-chloro-quinoline, 1-ethyl-3-carboethoxy-4-oxo-6-cyclohexyl-7-chloro-1,4-dihydroquinoline can be prepared; melting point 173°–174°C. (From methylene chloride/ether).

EXAMPLE 15

Starting from 3-carboethoxy-4-hydroxy-6-cycloheptyl-quinoline, 1-ethyl-3-carboethoxy-4-oxo-6-cycloheptyl-1,4-dihydroquinoline can be prepared; melting point 180°–181°C. (From methylene chloride/ether/hexane).

EXAMPLE 16

Starting from 3-carboethoxy-4-hydroxy-6-cyclohhexyl-quinoline, 1-ethyl-3-carboethoxy-4-oxo-6-cyclohexyl-1,4-dihydro-quinoline can be prepared; melting point 163°–165°C. (From water/dimethylformamide).

EXAMPLE 17

Starting from 3-carboethoxy-4-hydroxy-6-cyclopentyl-quinoline, 4-hydroxy-6-cyclopentyl-quinoline-3-carboxylic acid can be prepared analogously to the description in Example 2; melting point 252°–254°C, with decomposition.

EXAMPLE 18

Starting from 3-carboethoxy-4-hydroxy-6-cyclohexyl-7-chloro-quinoline, 4-hydroxy-6-cyclohexyl-7-chloro-quinoline-3-carboxylic acid can be prepared analogously to the description in Example 2; melting point 260°C, with decomposition. (From ethanol/water).

EXAMPLE 19

Starting from 3-carboethoxy-4-hydroxy-6-cycloheptyl-quinoline 4-hydroxy-6-cycloheptyl-quinoline-3-carboxylic acid can be prepared analogously to the description in Example 2; melting point >250°C, with decomposition. (From ethanol/water).

EXAMPLE 20

Starting from 3-carboethoxy-4-hydroxy-6-[adamantyl(1)]-quinoline, 4-hydroxy-6-[adamantyl-(1)]-quinoline-3-carboxylic acid can be prepared analogously to the description in Example 2; melting point 285°–287°C, with decomposition.

EXAMPLE 21

Starting from 3-carboethoxy-4-hydroxy-8-cyclohexyl-quinoline, 4-hydroxy-8-cyclohexyl-quinoline-3-carboxylic acid can be prepared analogously to the description in Example 2; melting point >250°C, with decomposition. (From ethanol).

EXAMPLE 22

Starting from 3-carboethoxy-4-hydroxy-6-cyclopentyl-quinoline 1-ethyl-4-oxo-6-cyclopentyl-1,4-dihydroquinoline-3-carboxylic acid can be manufactured analogously to the description in Example 3; melting point 185°–187°C. (From ethanol).

EXAMPLE 23

Starting from 3-carboethoxy-4-hydroxy-6-cyclohexyl-quinoline, 1-methyl-4-oxo-6-cyclohexyl-1,4-dihydro-quinoline-3-carboxylic acid can be manufactured analogously to the description in Example 3; melting point 258°–260°C. (From etthanol).

EXAMPLE 24

Starting from 3-carboethoxy-4-hydroxy-6-cyclohexyl-quinoline, 1-allyl-4-oxo-6-cyclohexyl-1,4-dihydro-quinoline-3-carboxylic acid can be manufactured analogously to the description in Example 3; melting point 175°–176°C, with decomposition. (From ethanol/water).

EXAMPLE 25

Starting from 3-carboethoxy-4-hydroxy-6-cyclohexyl-quinoline 1-benzyl-4-oxo-6-cyclohexyl-1,4-dihydroquinoline-3-carboxylic acid can be manufactured analogously to the description in Example 3; melting point 199°–201°C. (From ethanol/water).

EXAMPLE 26

Starting from 3-carboethoxy-4-hydroxy-6-[adamantyl-(1)]-quinoline, 1-ethyl-4-oxo-6-[adamantyl-(1)]-1,4-dihydroquinoline-3-carboxylic acid can be manufactured analogously to the description in Example 3; melting point 255°–257°C.

EXAMPLE 27

Starting from 3-carboethoxy-4-hydroxy-6-cyclohexyl-7-chloro-quinoline, 1-ethyl-4-oxo-6-cyclohexyl-7-chloro-1,4-dihydro-quinoline-3-carboxylic acid can be manufactured analogously to the description in Example 3; melting point 237°–238°C. (From ethanol).

EXAMPLE 28

Starting from 3-carboethoxy-4-hydroxy-6-cycloheptyl-quinoline, 1-ethyl-4-oxo-6-cycloheptyl-1,4-dihydro-quinoline-3-carboxylic acid can be manufactured analogously to the description in Example 3; melting point 142°–144°C. (From ethanol/water).

EXAMPLE 29

Starting from 3-carboethoxy-4-hydroxy-6-(cyclohexen-1-yl)-quinoline, 1-ethyl-4-oxo-6-(cyclohexen-1-yl)-1,4-dihydro-quinoline-3-carboxylic acid can be manufactured analogously to the description in Example 3; melting point 153°–155°C. (From ethanol).

EXAMPLE 30

Starting from 3-carboethoxy-4-hydroxy-8-cyclohexyl-quinoline, 1-methyl-4-oxo-8-cyclohexyl-1,4-dihydro-quinoline-3-carboxylic acid can be manufactured analogously to the description in Example 3; melting point 198°–200°C. (From ethanol).

EXAMPLE 31

Starting from 3-carboethoxy-4-hydroxy-6-cyclohexyl-quinoline 1-methyl-3-carboethoxy-4-oxo-6- cyclohexyl-1,4-dihydro-quinoline can be manufactured analogously to the description in Example 6; melting point 179°C. (From ether/methylene chloride).

EXAMPLE 32

Starting from 3-carboethoxy-4-hydroxy-6-cyclohexyl-quinoline, 1-allyl-3-carboethoxy-4-oxo-6-cyclohhexyl-1,4-dihydro-quinoline can be manufactured analogously to the description in Example 6; melting point 136°C. (From ether/methylene chloride).

EXAMPLE 33

9.2 g of 4-cyclohexyl-N-ethyl-N-(1'-oxo-2'-carboethoxy-ethyl)-anthranilic acid ethyl ester in 30 ml of absolute ethanol are added dropwise to a solution of 0.8 g of sodium in 25 ml of absolute ethanol at room temperature. The yellow solution is boiled for 3 hours under reflux. The resulting suspension is then freed from the ethanol in vacuo. The residue is dissolved in ice water and acidified with hydrochloric acid. The oil which separates out is extracted with methylene chloride and the methylene chloride solution is washed with water, dried over sodium sulphate, filtered and evaporated to dryness in vacuo. An oil is obtained, which is crystallised from 50 ml of iso-propanol. This gives 1-ethyl-4-hydroxy-7-cyclohexyl-carbostyril-3-carboxylic acid ethyl ester of melting point 99°–101°C (colourless crystals).

4-Cyclohexyl-N-ethyl-N-(1'-oxo-2'-carboethoxyethyl)-anthranilic acid ethyl ester, required as the starting material, can be obtained as follows:

6.5 g of 4-cyclohexyl-N-ethylanthranilic acid ethyl ester are dissolved in 70 ml of absolute benzene and introduced into a vessel together with 3.35 g of ethyldiisopropylamine. A solution of 3.9 g of chlorocarbonylacetic acid ethyl ester in 40 ml of absolute benzene is added dropwise to this solution at room temperature over the course of 30 minutes. After stirring for 7 hours at room temperature, a further 3.9 g of chlorocarbonylacetic acid ethyl ester in benzene are added dropwise over the course of 15 minutes and the mixture is stirred at room temperature for a further 15 hours. The benzene solution is washed with water, sodium bicarbonate solution and water, dried over anhydrous sodium sulphate, filtered and evaporated to dryness in vacuo. The product is thus obtained as a light yellow oil, whhich is converted further directly, without additional purification.

EXAMPLE 34

120 ml of diphenyl ether are added to 35.4 g of 3-cyclohexyl-4-methoxyanilinomethylenemalonic acid diethyl ester. The mixture is brought to the boil over the course of 10 minutes and diphenyl ether is slowly distilled off. Ethanol is first added to the hot residue, and after cooling ether is added. The crystals are filtered off, boiled up in methanol and filtered off. The crystalline product is thoroughly washed with methanol and ether. This gives 3-carboethoxy-4-hydroxy-6-methoxy-7-cyclohexyl-quinoline of melting point > 300°C.

The starting material can be prepared as follows:

19.4 g of 3-cyclohexyl-4-methoxyaniline and 20.5 g of ethoxymethylmalonic acid diethyl ester are warmed to 140°C in a distillation apparatus. The distillation residue (a dark oil) contains crude 3-cyclohexyl-4-methoxyanilinomethylenemalonic acid diethyl ester, which is cyclised directly without purification.

EXAMPLE 35

A suspension of 54 g of 3-carboethoxy-b 4-hydroxy-6-methoxy-7-cyclohexyl-quinoline and 9.5 g of sodium hydride (50% strength in mineral oil) in 500 ml of absolute dimethylformamide is stirred for 1 hour at room temperature with exclusion of water. The temperature of the reaction mixture rises to 30°C and a homogeneous solution is produced. The solution is then stirred for a further 30 minutes, at 50°C. 52 g of ethyl iodide are added dropwise over the course of 10 minutes to the cooled solution, whilst stirring, and the whole is stirred for 3 hours at 50–55°C.

The mixture is now cooled to room temperature and 1,500 ml of water are added slowly whilst stirring. The crystals are filtered off, washed with water and recrystallised from 200 ml of i-propanol and 400 ml of ether. 1-Ethyl-4-oxo-6-methoxy-7-cyclohexyl-1,4-dihydro-quinoline-3-carboxylic acid ethyl ester, thus obtained, melts at 154°–156°C. After a further recrystallisation from i-propanol/ether, the product melts at 158°–159°C.

EXAMPLE 36

A suspension of 18.7 g of 1-ethyl-4-oxo-6-methoxy-7-cyclohexyl-1,4-dihydro-quinoline-3-carboxylic acid ethyl ester described in Example 18, in 150 ml of ethanol and 150 ml of 2 N sodium hydroxide solution is boiled for 5 hours under reflux. The clear solution thereby produced is evaporated to dryness in vacuo. 2 N Hydrochloric acid is added to the residue. The resulting crystals are filtered off and well washed with water. 1-Ethyl-4-oxo-6-methoxy-7-cyclohexyl-1,4-dihydro-quinoline-3-carboxylic acid, thus obtained, melts at 176°–178°C.

EXAMPLE 37

14 g of 3-carboethoxy-4-hydroxy-6-cyclohexyl-quinoline are added to a solution of 1.45 g of sodium in 150 ml of absolute methanol, whilst stirring, and the mixture is heated to the boil for 1 hour, with exclusion of water. 7.15 g of benzyl chloride are then added dropwise to the reaction mixture, which is boiled for a further 5 hours under reflux. It is then evaporated to dryness in vacuo and the residue is partitioned between 4 times 500 ml of chloroform and 500 ml of 1 N potassium hydroxide solution at 0°C. The organic phases are washed with twice 500 ml of water, dried over sodium sulphate and evaporated to dryness in vacuo. Repeated crystallisation of the evaporation residue from ethanol gives 1-benzyl-3-carbomethoxy-4-oxo-6-cyclohexyl-1,4-dihydroquinoline of melting point 211°–213°C.

EXAMPLE 38

4.3 g of 1-ethyl-4-hydroxy-7-cyclohexyl-carbostyril-3-carboxylic acid ethyl ester and 1.75 g of p-chloroaniline in 200 ml of xylene are boiled under reflux (water separator). After 6 hours, the water separator is emptied completely, 100 ml of xylene are introduced and the mixture is then boiled for a further 15 hours under reflux. The xylene solution is concentrated in vacuo. The crystals which have separated out are filtered off and washed with xylene and petroleum ether. 1-Ethyl-4-hydroxy-7-cyclohexyl-carbostyril-3-(p-chlorocarboxanilide) of melting point 188°–90°C is obtained.

EXAMPLE 39

10 g of powdered 3-acetyl-4-hydroxy-7-cyclohexyl-quinoline are added to a solution of 10 ml of dioxane and 10 g of a freshly prepared hypochlorite solution at room temperature. After 45 minutes, the unconverted acetyl compound is washed out with chloroform. The aqueous solution is acidified with 10% strength hydrochloric acid. The product which precipitates is washed with water and then dried. 7-Cyclohexyl-4-hydroxy-quinoline-3-carboxylic acid of melting point 241°–43°C is obtained.

The starting material can be manufactured as follows:

61.6 g of 2-(m-cyclohexylanilino)-1-acetyl-acrylic acid ethyl ester in 200 ml of diphenyl ether are boiled for 30 minutes. The ethanol produced is distilled off at the same time. The diphenyl ether is then very largely distilled off. The solid residue is digested with 800 ml of ether and filtered off and the filter residue is washed with ethyl acetate and ether. 3-Acetyl-4-hydroxy-7-cyclohexyl-quinoline of melting point 274°–8°C (decomposition) is obtained.

EXAMPLE 40

Starting from 3-carboethoxy-4-hydroxy-6-cycloheptyl-quinoline and methyl iodide, 1-methyl-3-carboethoxy-4-oxo-6-cycloheptyl-1,4-dihydroquinoline of melting point 182°–183°C (from ethanol) is obtained analogously to the process described in Example 6.

EXAMPLE 41

Starting from 1-methyl-3-carboethoxy-4-hydroxy-6-cycloheptyl-1,4-dihydro-quinoline, 1-methyl-4-oxo-6-cycloheptyl-1,4-dihydroquinoline-3-carboxylic acid of melting point 253°–255°C (from methylene chloride/ether) is obtained analogously to the process described in Example 7.

EXAMPLE 42

Starting from 3-carboethoxy-4-hydroxy-6-cyclohexyl-quinoline and hexyl iodide, 1-hexyl-3-carboethoxy-4-oxo-6-cycloheptyl-1,4-dihydroquinoline is obtained, analogously to the process described in Example 6, as a viscous oil. IR: $\nu_{CO}$: 1,720 cm$^{-1}$(s), 1,680 cm$^{-1}$(s).

EXAMPLE 43

Starting from 1-hexyl-3-carboethoxy-4-oxo-6-cycloheptyl-1,4-dihydroquinoline, 1-hexyl-4-oxo-7-cycloheptyl-4-dihydroquinoline-3-carboxylic acid, melting point 85°–87°C, (from ether) is obtained analogously to the process described in Example 7.

EXAMPLE 44

Starting from (4-cyclooctyl-anilino)-methylenemalonic acid diethyl ester, 3-carboethoxy-4-hydroxy-6-cyclooctyl-quinoline of melting point 275°C (decomposition) can be obtained analogously to Example 1.

EXAMPLE 45

Starting from 3-carboethoxy-4-hydroxy-6-cyclooctyl-quinoline,4-hydroxy-6-cyclooctyl-quinoline-3-carboxylic acid of melting point 260°–262°C (decomposition) (from ethanol) can be obtained analogously to Example 2.

EXAMPLE 46

Starting from 4-hydroxy-6-cyclooctyl-quinoline-3-carboxylic acid and ethyl iodide, 1-ethyl-4-oxo-6-cyclooctyl-1,4-dihydro-quinoline-3-carboxylic acid of melting point 152°–154°C (from methylene chloride/ether) can be obtained analogously to Example 3.

EXAMPLE 47

The following compounds can also be prepared analogously to the description in Example 33:

a. 4-Hydroxy-7-cyclohexyl-carbostyril-3-carboxylic acid ethyl ester, melting point 228°–230°C.

b. 1-Methyl-4-hydroxy-7-cyclohexyl-6-methoxy-carbostyril-3-carboxylic acid ethyl ester, melting point 150°–153°C.

c. 4-Hydroxy-7-cyclohexyl-6-methoxy-carbostyril-3-carboxylic acid ethyl ester, melting point 254°–256°C.

d. 4-Hydroxy-6-cyclohexyl-carbostyril-3-carboxylic acid ethyl ester, melting point >300°C.

e. 4-Hydroxy-6-cycloheptyl-carbostyril-3-carboxylic acid ethyl ester, melting point 210°–212°C.

EXAMPLE 48

100 ml of 5 N sodium hydroxide solution are added to 13 g of 3-carboethoxy-4-amidinothio-6-cycloheptylquionoline, and the mixture is boiled for 4 hours under reflux in a nitrogen atmosphere. It is then cooled to room temperature and adjusted to pH 2 with concentrated hydrochloric acid, a saturated solution of 20 ml of sodium bisulphite is added and the precipitate formed is filtered off. Fractional crystallisation of the filter residue gives 3-carboxy-4-mercapto-6-cycloheptyl-quinoline of melting point 285°C (decomposition).

The starting material can be prepared as follows:

a. A solution of 100 g of 3-carboethoxy-4-hydroxy-6-cycloheptyl-quinoline in 670 ml of phosphorus oxychloride is boiled for 2½ hours under reflux, with exclusion of water. It is then evaporated to dryness in vacuo, the residue is partitioned between 3 times 500 ml of methylene chloride and 3 times 500 ml of 2 N sodium hydroxide solution and the organic solution is washed until neutral, dried over sodium sulphate and evaporated to dryness in vacuo. The evaporation residue is treated with active charcoal and then recrystallised twice from petroleum ether. 3-Carboethoxy-4-chloro-6-cycloheptyl-quinoline of melting point 61°–62°C is thus obtained.

b. A solution of 6.3 g of thiourea in 300 ml of methanol is added to a solution of 25 g of 3-carboethoxy-4-chloro-6-cycloheptyl-quinoline in 200 ml of ethanol and the mixture is left to stand for 2 days at room temperature. The crude 3-carboethoxy-4-amidinothio-6-cycloheptyl-quinoline-hydrochloride formed, of melting point 280°C (decomposition), is then filtered off.

3-Carboethoxy-4-chloro-6-cycloheptyl-quinoline, mentioned under a), can also be prepared as follows:

10 g of p-cycloheptyl-anilinomethylene-malonic acid diethyl ester are dissolved in 50 ml of phosphorus oxychloride, 0.2 g of polyphosphoric acid is added and the mixture is boiled for 2 hours under reflux, with exclusion of water. The mixture is then evaporated to dryness in vacuo, the evaporation residue is partitioned between 3 times 100 ml of methylene chloride and 3 times 100 ml of 2 N sodium hydroxide solution and the organic solution is washed until neutral, dried over sodium sulphate and evaporated to dryness in vacuo. The evaporation residue is treated with active charcoal and a little silica gel and crystallised from petroleum ether to give 3-carboethoxy-4-chloro-6-cycloheptyl-quinoline of melting point 61°–62°C.

EXAMPLE 49

4.4 g of potassium permanganate are added in portions, whilst stirring, to a solution of 3 g of 3-carboxy-4-mercapto-6-cycloheptyl-quinoline in 50 ml of 3 N sodium hydroxide solution at 100°C. After completion of the addition, the mixture is stirred for a further 3 hours at 120°C. It is now cooled to room temperature, filtered and acidified with concentrated hydrochloric acid. The crystals which precipitate are filtered off, washed with water until neutral and dried.

The filter residue is dissolved in ethanol and the solution is treated with active charcoal and a little silica gel, filtered and evaporated in vacuo. Repeated fractional crystallisation from ethanol-water gives 3-carboxy-4-hydroxy-6-cycloheptyl-quinoline of melting point 270°C (decomposition).

EXAMPLE 50

4 g of 4-hydroxy-6-methoxy-7-cyclohexylcarbostyril-3-carboxylic acid ethyl ester are suspended in 40 ml of 2 N sodium hydroxide solution and 100 ml of absolute ethanol. This suspension is boiled for 4 hours under reflux and is thereby converted into a solution. After removing the ethanol in vacuo, the aqueous solution is diluted with water and filtered and the filtrate is acidified with dilute hydrochloric acid. The precipitate is filtered off, washed with water and dried. Colourless crystals of 4-hydroxy-6-methoxy-7-cyclohexylcarbostyril-3-carboxylic of melting point >300°C are thus obtained.

EXAMPLE 51

14.2 g of N-ethyl-p-cycloheptylanilinocarbonyl-diethyl malonate in approx. 140 g of polyphosphoric acid are stirred for 2 hours at 130°C internal temperature. The hot mixture is poured onto ice water while stirring and the whole is stirred for a further 30 minutes. The oily precipitate is extracted with methylene chloride. The methylene chloride extracts are washed twice with water, combined, dried and evaporated. A highly viscous oil is obtained. This oil is taken up in toluene, which leaves a certain proportion of crystalline material undissolved (1-ethyl-4-hydroxy-6-cycloheptyl-carbostyril). After filtering off, the toluene filtrate is chromatographed on a 60-fold amount of silica gel. In addition to N-ethyl-p-cycloheptylaniline, 1-1-ethyl-4-hydroxy-6-cycloheptyl-carbostyril-3-carboxylic acid ethyl ester is isolated, as a viscous oil, by using methylene chloride and methylene chloride/ethyl acetate (9:1).

The starting material can be prepared as follows:
a. 25.2 g of crude N-ethyl-p-cycloheptylaniline and 16.5 g of diisopropylethylamine are first introduced into 250 ml of absolute toluene and the mixture is cooled to approx. 10°C. 63 ml of a 20% strength solution of phosgene in toluene are added dropwise over the course of 1 hour at 5°C to 10°C. After stirring for 1 hour at room temperature, 2½ hours at 40°C and 1 hour at 50°C, the mixture is diluted with toluene. The toluene solution is washed once with sodium carbonate solution and twice with water and is then dried over sodium sulphate. After evaporating the toluene in vacuo, an oil remains, which is caused to crystallise using petroleum ether. The 4-cycloheptyl-(N-chlorocarbonyl-N-ethyl)-aniline obtained is recrystallised from hexane, melting point 62°–64°C.

b. 12.5 g of diethyl malonate and 1.9 g of sodium are initially introduced into 160 ml of tetrahydrofurane. The mixture is stirred overnight at 50°–60°C, in the course of which the sodium is completely consumed. A solution of 4-cyclohexyl-(N-chlorocarbonyl-N-ethyl)-aniline in 70 ml of tetrahydrofurane is added dropwise at room temperature. The mixture is boiled for 15 hours under reflux and the tetrahydrofurane is then removed in vacuo. The yellow crystalline residue is taken up in water and the resulting alkaline solution is acidified with dilute hydrochloric acid. The solution which is now acid is extracted with methylene chloride. The combined methylene chloride extracts are dried over sodium sulphate. The solvent is removed in vacuo and the oily compound is chromatographed on a 15-fold amount of silica gel. N-Ethyl-p-cycloheptylanilino carbonyl-diethyl malonate is eluted, as a yellow oil, with methylene chloride and methylene chloride/ethyl acetate (8:2).

EXAMPLE 52

4.6 g of absolute ethanol are added dropwise to a fine suspension of 2.3 g of sodium in 500 ml of xylene and 17 g of diethylmalonate are then added, also dropwise. The mixture is stirred for 15 minutes at room temperature and after heating is distilled through a short Vigreux column until the distillation temperature has reached 138°C. The mixture is then cooled to 60°C internal temperature and a solution of 27.3 g of 1-ethyl-7 cyclohexylisatoic anhydride in 250 ml of dioxane is added. The mixture is stirred for 14 hours at 60°C–70°C and is concentrated in vacuo (until the dioxane has been removed completely) and the xylene solution is shaken with 1 N hydrochloric acid and with water and dried over sodium sulphate. The xylene solution is boiled for 7 hours under reflux (with separation of water). Every two hours, the water separator is emptied and fresh xylene is added. The xylene is removed in vacuo and the residue is purified chromatographically. This gives 1-ethyl-4-hydroxy-6-cyclohexyl-carbostyril-3-carboxylic acid ethyl ester of melting point 99°–100°C. The starting material can be prepared as follows:

10 g of 2-ethylamino-4-cyclohexylbenzoic acid of melting point 172°–74°C are boiled with 30 g of chloroformic acid ethyl ester for 20 hours under reflux. The reaction mixture is cooled and filtered and the filter residue is purified from acetone/petroleum ether. 1-Ethyl-7-cyclo-hexylisatoic anhydride of melting point 253°C (decomposition) is obtained.

EXAMPLE 53

A solution of 0.1 mol of lithium N-isopropylcyclohexylamide (Journ of Amer. Chem. Soc, 93,2318(1971)) in 100 ml of tetrahydrofurane is cooled with acetone/solid carbon dioxide. 4.5 g of ethyl acetate are then added dropwise. The mixture is stirred for 15 minutes at −78°C.

A solution of 2.2 g of N-ethyl-N-carboethoxy-2-(ethoxycarbonyloxy-carbonyl)-5-cyclohexyl-aniline in 70 ml of tetrahydrofurane is then added dropwise. After 30 minutes, 30 ml of 20% strength hydrochloric acid are added. After 15 minutes' stirring at room temperature, the organic phase is separated off, dried and evaporated. The residue is dissolved in 20 ml of dimethylformamide and the solution is added dropwise at room temperature to a suspension of sodium hydride (obtained from 10 g of 50% strength dispersion in oil, washed 3 times with pentane) in 60 ml of dimethylformamide. The mixture is stirred for a further 24 hours at room temperature. Water is then added dropwise to the mixture with external cooling, until the excess sodium hydride has been destroyed. The mixture is then poured onto ice and acidified with dilute hydrochloric acid. The product which precipitates is separated off and recrystallised. 1-Ethyl-4-hydroxy-7-cyclohexyl-carbostyril-3-carboxylic acid ethyl ester of melting point 98°–100°C is thus obtained.

The starting material can be prepared as follows:

A solution of 8.7 g of 2-ethylamino-4-cyclohexylbenzoic acid in 150 ml of chloroform is first prepared. 9.2 g of diisopropylethylamine are added thereto, following dropwise by a solution of 9.1 g of chloroformic acid ethyl ester in 90 ml of chloroform. The mixture is stirred at room temperature for 14 hours. The chloroform solution is decanted off and evaporated and the resulting crude N-ethyl-N-carboethoxy-2-(ethoxycarbonyloxy-carbonyl)-5-cyclohexyl-aniline is used further directly.

The examples which follow are intended to explain in more detail the preparation of pharmaceutical and cosmetic compositions. The active substances used are in particular the new compounds described in the preceding test as being particularly valuable.

EXAMPLE 54

Hand disinfectant: A solution of 3.00 g of active substance and 3.00 g of sodium sulphoricinoleate in 47.00 g of polyethylene glycol 400, and a solution of 7.00 g of sodium dodecyl-sulphate in 39.85 g of water, are prepared, the two solutions are mixed and 0.15 g of perfume is added to the mixture. The resulting liquid is dripped or sprayed onto the moist skin, and rubbed in.

EXAMPLE 55

Wound powder: 3.00 g of active substance are thoroughly mixed with 5.0 g of zinc oxide, 41.9 g of rice starch and 50.0 g of talc which is impregnated with 0.1 g of perfume, and the mixture is sieved through a suitable fine sieve and again mixed well.

EXAMPLE 56

Wound ointment: 3.0 g of active substance are ground with 3.0 g of medicinal paraffin and introduced into a mixture of 10.0 g of lanoline and 84.0 g of white petroleum jelly which has been fused at a moderate temperature, and the mixture is allowed to cool whilst stirring.

EXAMPLE 57

Lozenges for disinfection of the mouth and throat: 50.0 g of active substance are carefully mixed with 400.0 g of caster sugar and at the same time moistened with a granulating solution of 8.0 g of gelatine and 2.0 g of glycerine in approx. 120 ml of water. The mass is granulated by passing through a suitable sieve, and the granules are dried. A sieved mixture of 3.0 g of highly disperse silica, 4.0 g of magnesium stearate, 0.7 g of aroma substances and 42.3 g of talc is added to the dried granules, the whole is thoroughly mixed and 1,000 tablets are pressed from the mixture.

EXAMPLE 58

Concentrate for a gargle: 5.0 g of active substance are dissolved in 60.0 g of 96% strength ethanol, 15.0 g of glycerine and 0.3 g of aroma substances are added and the solution is made up to 100.0 g with 19.7 g of distilled water. For gargling, approx. 5–20 drops of this concentrate are used in water.

EXAMPLE 59

Tablets

To prepare 1,000 tablets each containing 150 mg of active substance, 150.0 g of active substance are first thoroughly mixed with 60.0 g of maize starch and 35.0 g of lactose and the mixture is uniformly moistened with a granulating solution prepared from 5.0 g of gelatine and 3.0 g of glycerine in approx. 70 g of water. The mass is granulated by passing through a suitable sieve and is dried. The granules are thoroughly mixed with a sieved mixture of 15.0 g of talc, 10.0 g of dried maize starch and 2.0 g of magnesium stearate and 1,000 tablets are pressed from the mixture.

EXAMPLE 60

Dragées

To prepare 1,000 dragée cores, 150.0 g of active substance are first thoroughly mixed with 60.0 g of maize starch and 34.0 g of lactose, the whole is mixed with a paste of 6.0 g of starch, 3.0 g of glycerine and approx. 54 g of distilled water and the resulting mass is granulated by passing through a suitable sieve, and is dried. The granules are thoroughly mixed with a sieved mixture of 15.0 g of talc, 10.0 g of maize starch and 2.0 g of magnesium stearate and 1,000 dragée cores each weighing 280 mg are pressed from the mixture.

The above cores are coated, in a dragée-coating kettle, with a layer of the following composition: Shellac 2.000 g, gum arabic 7.500 g, dyestuff 0.180 g, highly disperse silica 2.000 g, talc 35.000 g, sugar 58.320 g. 1,000 dragées each weighing 385 mg and each containing 150 mg of active substance are obtained.

We claim:

1. A product of the formula

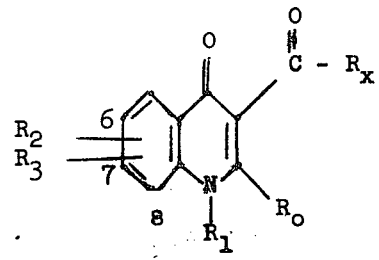

wherein $R_o$ denotes hydrogen or hydroxy, $R_1$ denotes hydrogen, alkyl, aklenyl or phenyl-alkyl having up to 8 carbon atoms $R_2$ is bound in the positions 6, 7 or 8 of the quinoline moiety and represents cycloalkyl or cycloalkenyl with 5–8 ring members, or 1-adamantyl, $R_3$ denotes lower alkyl, halogen or hydrogen and $R_x$ denotes hydroxy, alkoxy with up to 8 carbon atoms, amino, N-mono-lower alkylamino, N,N-di-lower alkylamino or anilino, wherein the term "lower" denotes said moieties having up to 4 carbon atoms; or a tautomeric form thereof, or a therapeutically acceptable salt thereof.

2. A product as claimed in claim 1 in which formula $R_0$ represents hydrogen or hydroxy, $R_1$ denotes hydrogen, $C_1$-$C_4$-alkyl, $C_3$-$C_4$-alkenyl or -phenyl-$C_1$-$C_2$-alkyl-, $R_2$ denotes cycloalkyl or cycloalkenyl with 5 to 8 ring members or 1-adamantyl bound in 6-, 7- or 8-position of the quinoline moiety, $R_3$ denotes hydrogen or halogen and $R_x$ denotes hydroxy, $C_1$-$C_3$-alkoxy or anilino; or a tautomeric form thereof.

3. A compound as claimed in claim 1 and being the 8-cyclohexyl-1-methyl-4-oxo-1,4-dihydro-quinoline-3-carboxylic acid, or a therapeutically acceptable salt thereof.

4. A compound as claimed in claim 1 and being the 6-cyclohexyl-1-ethyl-4-oxo-1,4-dihydro-quinoline-3-carboxylic acid, or a therapeutically acceptable salt thereof.

5. A compound as claimed in claim 1 and being the 6-cyclohexyl-4-hydroxy-quinoline-3-carboxylic acid ethyl ester, or a therapeutically acceptable salt thereof.

6. A compound as claimed in claim 1 and being the 6-cyclohexyl-4-hydroxy-quinoline-3-carboxylic acid, or a therapeutically acceptable salt thereof.

7. A compound as claimed in claim 1 and being the 7-cyclohexyl-4-hydroxy-quinoline-3-carboxylic acid, or a therapeutically acceptable salt thereof.

8. A compound as claimed in claim 1 and being the 7-cyclohexyl-1-ethyl-4-oxo-1,4-dihydro-quinoline-3-carboxylic acid, or a therapeutically acceptable salt thereof.

9. A compound as claimed in claim 1 and being the 8-cyclohexyl-4-hydroxy-quinoline-3-carboxylic acid, or a therapeutically acceptable salt thereof.

10. A compound as claimed in claim 1 and being the 6-cycloheptyl-1-ethyl-4-oxo-1,4-dihydro-quinoline-3-carboxylic acid ethyl ester, or a therapeutically acceptable salt thereof.

11. A compound as claimed in claim 1 and being the 7-chloro-6-cyclohexyl-1-ethyl-4-oxo-1,4-dihydro-3-carboxylic acid, or a therapeutically acceptable salt thereof.

* * * * *